(12) United States Patent
Sasagawa et al.

(10) Patent No.: US 11,837,105 B2
(45) Date of Patent: Dec. 5, 2023

(54) PSEUDO FOOD TEXTURE PRESENTATION DEVICE, PSEUDO FOOD TEXTURE PRESENTATION METHOD, AND PROGRAM

(71) Applicant: Nippon Telegraph and Telephone Corporation, Tokyo (JP)

(72) Inventors: Mana Sasagawa, Tokyo (JP); Arinobu Niijima, Tokyo (JP); Ryosuke Aoki, Tokyo (JP); Tomoki Watanabe, Tokyo (JP); Tomohiro Yamada, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 644 days.

(21) Appl. No.: 16/971,861

(22) PCT Filed: Feb. 21, 2019

(86) PCT No.: PCT/JP2019/006603
§ 371 (c)(1),
(2) Date: Aug. 21, 2020

(87) PCT Pub. No.: WO2019/163908
PCT Pub. Date: Aug. 29, 2019

(65) Prior Publication Data
US 2020/0402418 A1     Dec. 24, 2020

(30) Foreign Application Priority Data

Feb. 23, 2018 (JP) .................................. 2018-031268
Aug. 13, 2018 (JP) .................................. 2018-152335

(51) Int. Cl.
*A61B 5/03* (2006.01)
*G09B 19/00* (2006.01)
(Continued)

(52) U.S. Cl.
CPC .............. *G09B 19/00* (2013.01); *A61B 5/038* (2013.01); *A61B 5/1114* (2013.01);
(Continued)

(58) Field of Classification Search
None
See application file for complete search history.

(56) References Cited

U.S. PATENT DOCUMENTS

2006/0064037 A1* 3/2006 Shalon ................. A61B 5/0031
                                                            128/903
2009/0123886 A1* 5/2009 Vaska ..................... A61F 5/566
                                                            433/91
2013/0296751 A1* 11/2013 Martin ................. A63B 21/028
                                                            601/148

OTHER PUBLICATIONS

Brown et al., "Universal Robotic Gripper Based on the Jamming of Granular Material," PNAS, Nov. 2010, 107(44):18809-18814.
(Continued)

*Primary Examiner* — Bruk A Gebremichael
(74) *Attorney, Agent, or Firm* — Fish & Richardson P.C.

(57) ABSTRACT

The number n of times of chewing is counted by chewing number of times calculation means ($13b_2$) based on a change in the distance l from a photoreflector (50), which is received together with time t by measurement value receiving means ($13b_1$). To vary hardness h of a bag (30) to a stage that can be sensed, according to the number n of times of chewing, a required air pressure is set according to the current number n of times, based on a hardness/air pressure correspondence recording unit (13g) in which stages that have a significant difference therebetween and are stored in association with the number n of times of chewing are recorded. To realize the set air pressure inside the bag (30), the amount of sucking performed using a vacuum pump 20 is controlled by air pressure control means ($13b_4$).

20 Claims, 24 Drawing Sheets

(51) Int. Cl.
  *G06F 3/14* (2006.01)
  *A61B 5/00* (2006.01)
  *A61B 5/11* (2006.01)

(52) U.S. Cl.
  CPC .............. *A61B 5/1123* (2013.01); *A61B 5/42* (2013.01); *A61B 5/4547* (2013.01); *G06F 3/14* (2013.01)

(56) References Cited

OTHER PUBLICATIONS

Chi2018.acm.org, [online], "Technical Program—CHI 2018—Engage with CHI," Apr. 21-26, 2018, retrieved on Jun. 6, 2018, retrieved from URL<https://chi2018.acm.org/technical-program/?sessionId=-L96u7iVIwyazSpIXy75&publicationId=-L96tc50nExomgzMRVR>, 50 pages.

Confman.interaction-ipsj.org, [online], "Virtual Doll House Expanding Real-World Doll Play and Its Evaluation," 2018, retrieved on Jun. 20, 2018, retrieved from URL<https://confman.interaction-ipsj.org/cacheimg/i2018/export/webcat_1>, 51 pages (with English Translation).

Interaction-ipsj.org, [online], "Interaction 2018: Interaction 2018 The 22 Symposium of the Information Processing Society of Japan," Mar. 5-7, 2018, retrieved on Jun. 6, 2018, retrieved from URL<http://www.interaction-ipsj.org/2018/program/>, 57 pages (with English Translation).

Iwata et al., "Food Simulator: A Haptic Interface for Biting," Proceedings of the 2004 Virtual Reality (VR'04), Mar. 27-31, 2004, pp. 51-57.

Sasagawa et al., "A Proposal of Food Texture Display by Jamming (Abstract)," CHI 2018, Apr. 21-26, 2018, 6 pages.

Sasagawa et al., "A Proposal of Food Texture Display by Jamming (Literature)," NTT Service Evolution Laboratories, NTT Corporation, Apr. 21, 2018, 1 page.

Sasagawa et al., "Texture Presentation System Using Jamming Transition," Information-Processing Society Interaction, Mar. 5, 2018, 9 pages (with English Translation).

\* cited by examiner

Fig. 6

| 7 STAGES PRESENTED IN SENSORY EVALUATION | STAGE1 | STAGE2 | STAGE3 | STAGE4 | STAGE5 | STAGE6 | STAGE7 |
|---|---|---|---|---|---|---|---|
| 4 STAGES BETWEEN WHICH HARDNESS DIFFERENCE CAN BE SENSED | 1 | 2 | | 3 | | | 4 |
| AIR PRESSURE (kPa) | 0 | -10 | -20 | -30 | -40 | -50 | -60 |

13g

13h

PSEUDO FOOD TEXTURE PRESENTATION DEVICE, PSEUDO FOOD TEXTURE PRESENTATION METHOD, AND PROGRAM

CROSS-REFERENCE TO RELATED APPLICATIONS

This application is a National Stage application under 35 U.S.C. § 371 of International Application No. PCT/JP2019/006603, having an International Filing Date of Feb. 21, 2019, which claims priority to Japanese Application Serial No. 2018-152335, filed on Aug. 13, 2018 and Japanese Application Serial No. 2018-031268, filed on Feb. 23, 2018. The disclosure of the prior application is considered part of the disclosure of this application, and is incorporated in its entirety into this application.

TECHNICAL FIELD

The present invention relates to a mock food texture presenting apparatus, a method for presenting mock food texture, and a program.

BACKGROUND ART

Studies for presenting food texture have been made and application of the studies to chewing training, entertainment, food design, etc. has been considered (see NPL 1, for example). Food texture is physical properties of food felt in the mouth. Therefore, to present food texture, it is important to present hardness and the shape of a food in the mouth of a user.

There is a conventional technology that uses a physical phenomenon called jamming transition to present hardness and the shape. The jamming transition is a physical phenomenon in which a powder or granular material behaves differently depending on the density, i.e., behaves like a solid when the density of the powder or granular material is high and behaves like a fluid when the density is low.

A technology that applies the lamming transition to a robot hand is proposed as one example of studies utilizing the jamming transition. For example, NPL 2 proposes a method for holding an object using a robot hand that is constituted by a powder or granular material by pressing the robot hand in a soft state against the object, deforming the robot hand along the shape of the object, and making the robot hand hard when the robot hand has conformed to the shape of the object.

CITATION LIST

Non Patent Literature

[NPL 1] Hiroo Iwata, Hiroaki Yano, Takahiro Uemura, and Tetsuro Moriya. 2004. Food Simulator: A Haptic Interface for Biting. In Proc. of VR '04. 51-57.
[NPL 2] Eric Brown, Nicholas Rodenberg, John Amend, Annan Mozeika, Erik Steltz, Mitchell R. Zakin, Hod Lipson, and Heinrich M. Jaeger. 2010. Universal robotic gripper based on the jamming of granular material. Proc. of the National Academy of Sciences 107, 44 (2010), 18809-18814.

SUMMARY OF THE INVENTION

Technical Problem

It has been difficult to present hardness and a shape in the mouth based on the content disclosed by NPL 1.

On the other hand, NPL 2 describes a method for holding an object depending only on whether or not to cause the jamming transition. However, NPL 2 does not mention about a technology for causing the jamming transition by controlling the density of a powder or granular material according to conditions of actions performed on an object by a user with their mouth (hereinafter referred to as "conditions of actions of a user"), e.g., conditions of actions, such as chewing, biting off, crushing (mastication), grinding with teeth, licking with the tongue, rolling in the mouth, sandwiching with teeth, lips, the tongue, etc., and pressing with the tongue, that a user performs on a food in their mouth.

The present invention was made in view of the foregoing issue, and it is an object of the present invention to provide a mock food texture presenting apparatus, a method for presenting mock food texture, and a program that make it possible to control the density of a powder or granular material according to conditions of actions of a user to enable presentation of food texture by presenting hardness and a shape using the jamming transition.

Means for Solving the Problem

A mock food texture presenting apparatus according to a first aspect of the present invention includes an enclosing body that encloses a powder or granular material and has hardness that varies according to an air pressure inside the enclosing body, chewing condition grasp means for grasping conditions of chewing performed on the enclosing body by a user, and enclosing body control means for controlling density of the powder or granular material in the enclosing body according to the conditions of chewing grasped by the chewing condition grasp means.

A mock food texture presenting apparatus according to a second aspect of the present invention includes an enclosing body that encloses a powder or granular material, measurement means for measuring the number of times a user has licked the enclosing body with their tongue, and control means for controlling density of the powder or granular material in the enclosing body according to the measured number of times.

A mock food texture presenting apparatus according to a third aspect of the present invention includes an enclosing body that encloses a powder or granular material, measurement means for measuring a rotation amount of the enclosing body, and control means for controlling density of the powder or granular material in the enclosing body according to the measured rotation amount.

A mock food texture presenting apparatus according to a fourth aspect of the present invention includes an enclosing body that encloses a powder or granular material, measurement means for measuring pressure applied to the enclosing body from the outside, and control means for controlling density of the powder or granular material in the enclosing body according to the measured pressure.

Effects of the Invention

According to each of the first to fourth aspects of the present invention, the powder or granular material is enclosed in the enclosing body, and the hardness of the enclosing body can be adjusted through the jamming transition by controlling the density of the powder or granular material in the enclosing body.

According to the first aspect, the density of the powder or granular material in the enclosing body is controlled according to conditions of chewing performed on the enclosing body by a user. Therefore, food texture as if the hardness of a food varies as the food is chewed can be presented to the user.

According to the second aspect, the density of the powder or granular material in the enclosing body is controlled according to the number of times a user has licked the enclosing body with their tongue. Therefore, food texture as if the hardness of a food varies as the food is licked with the tongue can be presented to the user.

According to the third aspect, the density of the powder or granular material in the enclosing body is controlled according to the rotation amount of the enclosing body. Therefore, food texture as if the hardness of a food varies as the food is rolled in the mouth can be presented to the user.

According to the fourth aspect, the density of the powder or granular material in the enclosing body is controlled according to pressure applied to the enclosing body from the outside. Therefore, food texture as if the hardness of a food varies as the food is sandwiched between teeth, lips, the tongue, etc., or pressured with the tongue can be presented to the user.

Namely, according to the present invention, it is possible to provide a technology that makes it possible to control the density of a powder or granular material according to conditions of actions of a user to enable presentation of food texture by presenting hardness and a shape using the jamming transition.

BRIEF DESCRIPTION OF DRAWINGS

FIG. 6 is a database that is recorded in the hardness/air pressure correspondence recording unit provided in the mock food texture presenting apparatus shown in FIG. 1 and shows a relationship between a combination of stages between which a user can recognize a largest number of hardness difference most frequently and air pressures that are required to present the respective stages.

DESCRIPTION OF EMBODIMENTS

The following describes mock food texture presenting apparatuses, methods for presenting mock food texture, and programs according to embodiments of the present invention.

First Embodiment

Figure 1:
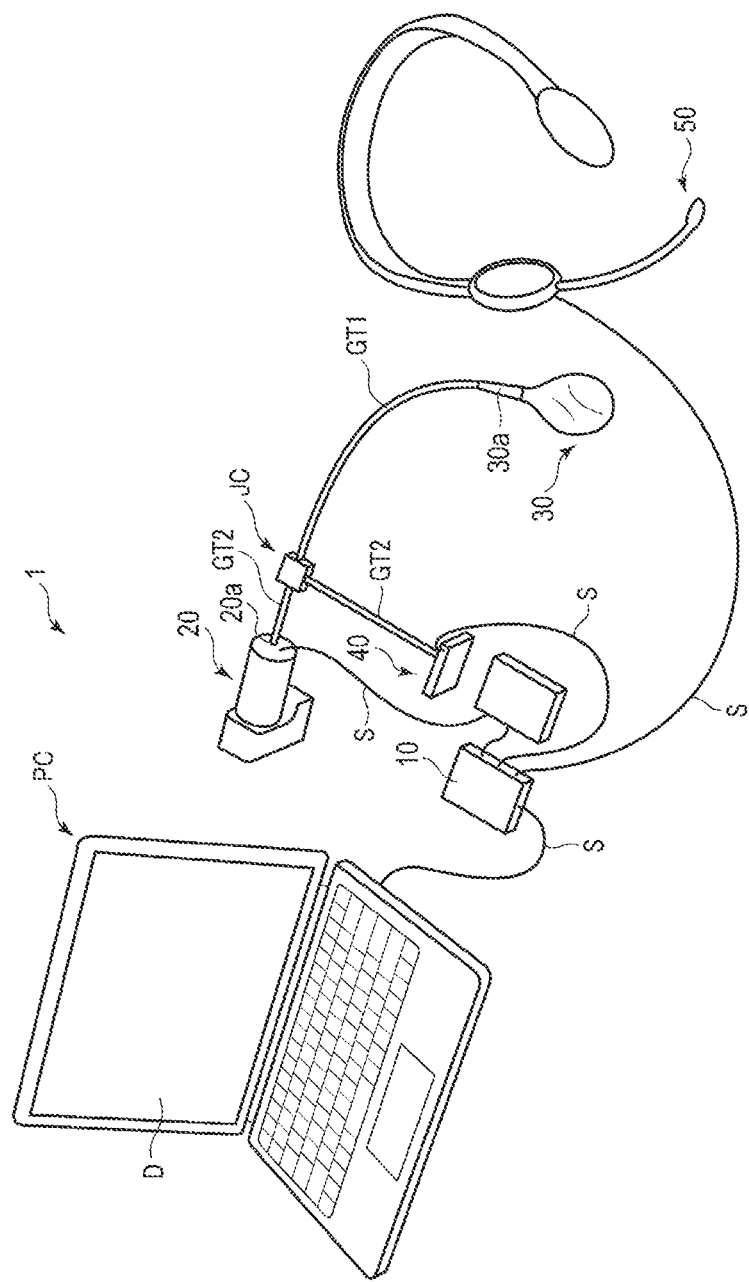
FIG. 1 is a diagram showing the overall configuration of a mock food texture presenting apparatus according to a first embodiment.

FIG. 1 is a diagram showing the overall configuration of a mock food texture presenting apparatus 1 according to a first embodiment. The mock food texture presenting apparatus 1 includes a microcomputer 10, a vacuum pump 20, a bag 30, which is an enclosing body, a negative pressure sensor 40, a photoreflector 50, and a personal computer PC.

The present embodiment is constituted by two processes. A first process is a process (hereinafter referred to as a "database creation process") for creating a database that is necessary to present various shapes of the bag 30 and different food textures (degrees of hardness h) of the bag 30 through the jamming transition by controlling the density of a powder or granular material in the bag 30 according to conditions of chewing performed by a user 60 on the bag 30 held in the mouth of the user 60. A second process is a mock food texture presenting process for presenting various shapes of the bag 30 and different food textures (degrees of hardness h) of the bag 30 using the database created in the database creation process.

The following describes a configuration for realizing the database creation process and the mock food texture presenting process.

The vacuum pump 20 includes a suction opening 20a for sucking air, and the suction opening 20a and an air opening 30a of the bag 30 are connected to each other via a junction portion JC using a flexible tube GT1 made of polyurethane and a flexible tube GT2 constituted by an acrylic pipe and a silicone hose, for example.

A motor is provided in the vacuum pump 20, and the amount of air sucked from the bag 30 is adjusted (controlled) by controlling the number of revolution of the motor by controlling the duty ratio of a Pulse Width Modulation (PWM) signal for driving the motor.

The bag 30 is constituted by a deformable (stretchable) material, such as rubber, having the shape of a bag (in this example, rubber balloon), and a powder or granular material, such as coffee powder, is contained in the bag 30. The bag 30 presents various degrees of hardness depending on the air quantity (degree of vacuum [kPa]) when sucking is performed using the vacuum pump 20.

The negative pressure sensor 40 is connected to the junction portion JC via a flexible tube GT2, for example, and has a function of sensing the air pressure [kPa] inside the bag 30.

The photoreflector 50 is provided using a headphone-type wearing member that is to be put on the head of the user 60, for example, and has a function of measuring a distance l from the photoreflector 50 to a lower jaw lj portion of the user.

The microcomputer 10 is connected to the vacuum pump 20, the negative pressure sensor 40, the photoreflector 50, and the personal computer PC using signal lines S. Note that wireless communication may also be used instead of wired communication.

The personal computer PC includes a display unit D and has a function of receiving various kinds of measurement data (measurement data such as data of the air pressure inside the bag 30 and data of the distance to the lower jaw lj) from the microcomputer 10 and outputting the measurement data, graphs etc., obtained by processing the measurement data, to the display unit D.

Figure 2:
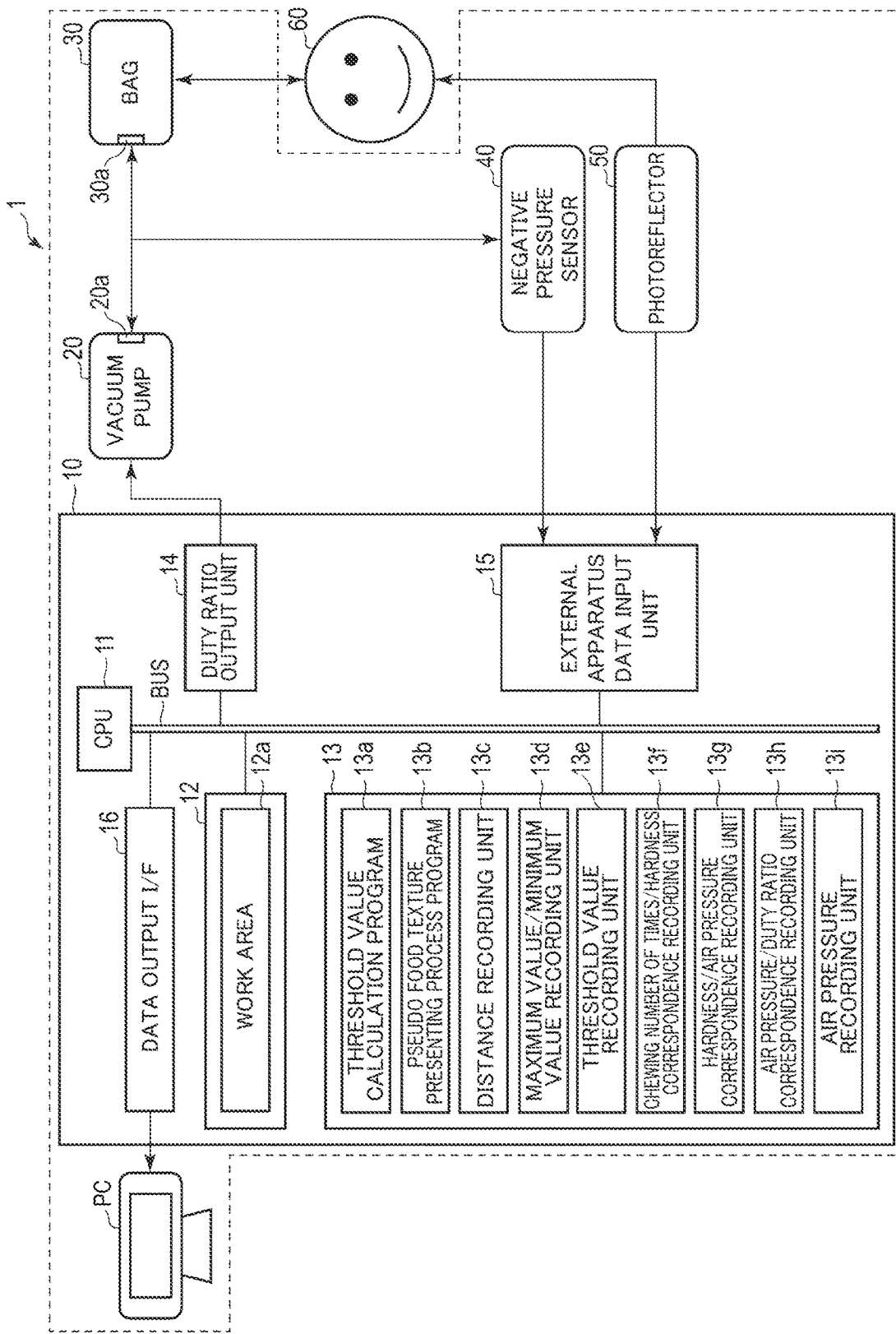
FIG. 2 is a block diagram focused on a functional configuration of a microcomputer in the mock food texture presenting apparatus shown in FIG. 1.

FIG. 2 is a block diagram focused on a functional configuration of the microcomputer 10 in the mock food texture presenting apparatus 1.

The microcomputer 10 includes a CPU (Central Processing Unit) 11 as a control unit.

The CPU 11 is connected to a RAM (Random Access Memory) 12, a recording unit 13, a duty ratio output unit 14, an external apparatus data input unit 15, and a data output interface (I/F) 16 via a system BUS.

The RAM 12 includes a work area 12a. The recording unit 13 is constituted by a hard disk, a flash memory, etc., and includes a program area in which a threshold value calculation program 13a to be used for creating a database and a mock food texture presenting process program 13b are stored, a distance recording unit 13c, a maximum value/minimum value recording unit 13d, a threshold value recording unit 13e, a chewing number of times/hardness correspondence recording unit 13f, a hardness/air pressure correspondence recording unit 13g, an air pressure/duty ratio correspondence recording unit 13h, and an air pressure recording unit 13i.

The threshold value calculation program 13a and the mock food texture presenting process program 13b are each activated and executed by the CPU 11 using the work area 12a, and as a result of operations of circuit units being controlled in accordance with control signals output by the CPU 11 based on the threshold value calculation program 13a and the mock food texture presenting process program 13b, the database creation process and the mock food texture presenting process, which will be described later, are realized.

The distance recording unit 13c records the distance l between the photoreflector 50 and the lower jaw lj of the user 60 measured using the photoreflector 50, in association with a time t at which the distance l is measured.

A maximum value lmax and a minimum value lmin of the distance l between the photoreflector 50 and the lower jaw lj of the user 60 are stored in the maximum value/minimum value recording unit 13d in advance.

A threshold value lth that is calculated using the threshold value calculation program 13a based on the maximum value lmax and the minimum value lmin recorded in the maximum value/minimum value recording unit 13d is recorded in the threshold value recording unit 13e in advance.

A correspondence table (database) in which the number n of times of chewing performed on the bag 30 by the user 60 is associated with the hardness h of the bag 30 is recorded in the chewing number of times/hardness correspondence recording unit 13f in advance. The correspondence table is set such that, as the number n of times of chewing is increased, the hardness h of the bag 30 is reduced, for example.

Assume that the hardness h of the bag 30 can be set to Stage 1 to Stage 7 according to the air pressure (0 [kPa] to −60 [kPa]) inside the bag 30 that can be realized by performing sucking using the vacuum pump 20 (for example, Stage 1 represents hardness at a time when the air pressure is 0 [kPa], Stage 2 represents hardness at a time when the air pressure is −10 [kPa], Stage 3 represents hardness at a time when the air pressure is −20 [kPa], Stage 4 represents hardness at a time when the air pressure is −30 [kPa], Stage 5 represents hardness at a time when the air pressure is −40 [kPa], Stage 6 represents hardness at a time when the air pressure is −50 [kPa], and Stage 7 represents hardness at a time when the air pressure is −60 [kPa]).

As the numeral becomes small (for example, Stage 1), the hardness h of the bag 30 is reduced and food texture becomes soft, and as the numeral becomes large (for example, Stage 7), the hardness h of the bag 30 is increased and food texture becomes hard, for example.

A correspondence table (database) in which the stages (Stage 1 to Stage 7) of the hardness h of the bag 30 are associated with air pressures [kPa] required to achieve the hardness h of the respective stages is recorded in the hardness/air pressure correspondence recording unit 13g in advance.

A correspondence table (database) in which the air pressure [kPa] inside the bag 30 is associated with the duty ratio

[%] of a PWM signal is recorded in the air pressure/duty ratio correspondence recording unit 13h in advance.

The air pressure recording unit 13i records the air pressure [kPa] inside the bag 30 in real time when the bag is chewed by the user 60.

Note that methods for creating databases that are recorded in advance in the threshold value recording unit 13e, the hardness/air pressure correspondence recording unit 13g, and the air pressure/duty ratio correspondence recording unit 13h will be described later.

The duty ratio output unit 14 outputs a PWM signal that has a prescribed duty ratio [%] to the vacuum pump 20 in response to the above-described control signal. Thus, the amount of sucking (degree of vacuum) from the bag 30 performed using the vacuum pimp 20 is adjusted (controlled).

The external apparatus data input unit 15 receives the air pressure [kPa] inside the bag 30 from the negative pressure sensor 40 and receives the distance l between the lower jaw lj of the user 60 and the photoreflector 50 from the photoreflector 50.

The data output I/F 16 outputs various kinds of data, such as data regarding the air pressure [kPa] inside the bag 30 received from the negative pressure sensor 40 and data regarding the distance l from the photoreflector 50, to the personal computer PC. Specifically, various kinds of data recorded in the distance recording unit 13c, the maximum value/minimum value recording unit 13d, the threshold value recording unit 13e, the chewing number of times/hardness correspondence recording unit 13f, the hardness/air pressure correspondence recording unit 13g, the air pressure/duty ratio correspondence recording unit 13h, and the air pressure recording unit 13i, which are provided in the recording unit 13, are output via the data output I/F 16 to the personal computer PC. As a result, the various kinds of data and tables, graphs, etc., (FIGS. 5, 6, 7, and 9) that are obtained by processing the various kinds of data are displayed in the display unit D of the personal computer PC.

Figure 3:
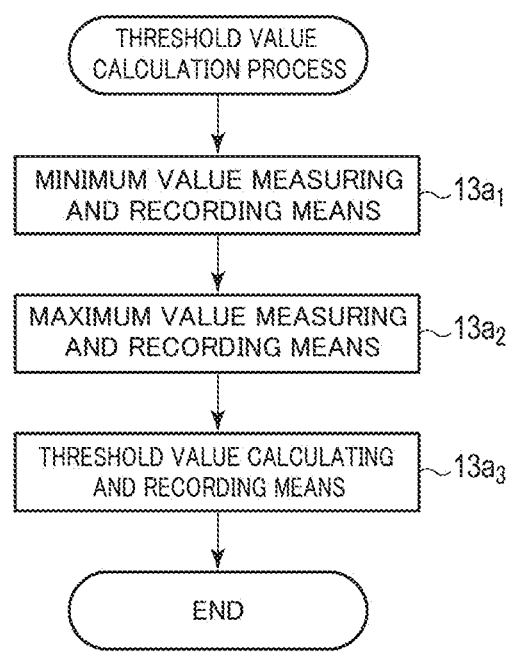
FIG. 3 is a block diagram showing a threshold value calculation process realized by the mock food texture presenting apparatus shown in FIG. 1.

As a result of the CPU 11 controlling operations of circuit units following instructions described in the threshold value calculation program 13a, which is used for creating a database, and software and hardware operating in cooperation with each other, the mock food texture presenting apparatus 1 configured as described above realizes a threshold value calculation process, which is a process for creating a database as described below with reference to FIG. 3. Similarly, as a result of the CPU 11 controlling operations of circuit units following instructions described in the mock food texture presenting process program 13b and software and hardware operating in cooperation with each other, the mock food texture presenting apparatus 1 realizes a mock food texture presenting process as described below with reference to FIG. 8.

Database Creation Process

The following first describes the threshold value calculation process as a database creation process. FIG. 3 is a block diagram showing the threshold value calculation process realized by the mock food texture presenting apparatus 1.

Namely, the CPU 11 functions as minimum value measuring and recording means $13a_1$, maximum value measuring and recording means $13a_2$, and threshold value calculating and recording means $13a_3$, following the threshold value calculation program 13a.

Figure 4A:
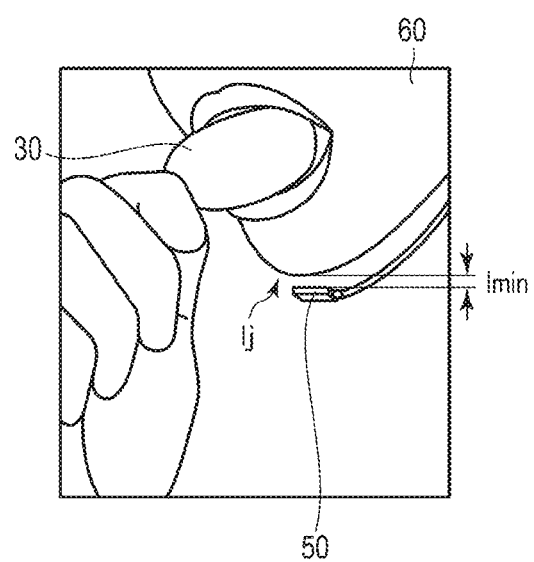
FIG. 4A is a diagram showing a state in which a distance (minimum distance lmin) between a photoreflector provided in the mock food texture presenting apparatus shown in FIG. 1 and the lower jaw of a user is measured.
Figure 4B:
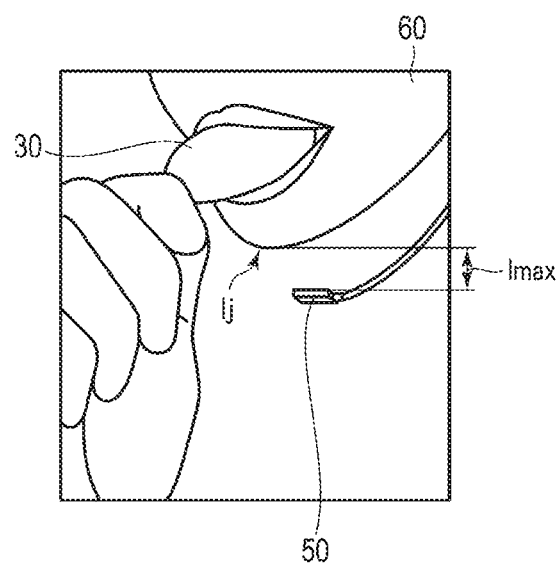
FIG. 4B is a diagram showing a state in which a distance (maximum distance lmax) between the photoreflector provided in the mock food texture presenting apparatus shown in FIG. 1 and the lower jaw of a user is measured.

FIGS. 4A and 4B are diagrams showing states in which the distance (minimum distance, maximum distance) between the photoreflector 50 and the lower jaw lj of the user 60 is measured.

As shown in FIG. 4A, the minimum value measuring and recording means $13a_1$ measures the distance lmin between the photoreflector 50 and the lower jaw lj when the mouth is opened to the maximum extent to chew the bag 30, and records the measured distance lmin in the maximum value/minimum value recording unit 13d.

Also, as shown in FIG. 4B, the maximum value measuring and recording means $13a_2$ measures the distance lmax between the photoreflector 50 and the lower jaw lj when the mouth is closed to the minimum extent to chew the bag 30, and records the measured distance lmax in the maximum value/minimum value recording unit 13d.

Then, the threshold value calculating and recording means $13a_3$ calculates a threshold value lth from the distance lmin and the distance lmax recorded in the maximum value/minimum value recording unit 13d, e.g., calculates an average value of the distance lmin and the distance lmax as the threshold value lth, and records the calculated threshold value lth in the threshold value recording unit 13e.

Next, methods for creating databases that are recorded in advance in the hardness/air pressure correspondence recording unit 13g and the air pressure/duty ratio correspondence recording unit 13h will be described in order.

The following describes a method for creating a database for the hardness/air pressure correspondence recording unit 13g. The following separately describes a preliminary process for creating the database for the hardness/air pressure correspondence recording unit 13g and a method for creating the database to be recorded in the hardness/air pressure correspondence recording unit 13g based on a result obtained in the preliminary process.

First, the preliminary process (1. experiment conditions, 2. experiment method, 3. experiment result) for creating the database for the hardness/air pressure correspondence recording unit 13g will be described. By referring to a result obtained in this preliminary process, it is possible to determine whether or not the user 60 can sense a hardness difference between a plurality of stages representing different degrees of hardness h, in their mouth.

1. Experiment Conditions

First, the air pressure inside the bag 30 is varied from 0 [kpa] to −60 [kPa] by sucking air from the bag 30 using the vacuum pump 20, to vary the hardness h of the bag 30 from Stage 1 to Stage 7.

Then, the hardness is compared between different stages (for example, between the hardness h of Stage 1 and the hardness h of Stage 2) that are set using the vacuum pump 20, by using an experiment method described later. The Scheffe's method of paired comparisons is used to compare the hardness. Namely, two different degrees of hardness h are imparted to the same bag 30, and the user 60, who is the subject, chews the bag 30 with the two different degrees of hardness h (for example, Stage 1 and Stage 2) in order, and evaluates in which case, the bag 30 is hard to what extent, using levels. This is performed for every combination of stages to be evaluated.

Note that it is also possible to prepare two bags 30 having different degrees of hardness h and cause the subject to chew the two bags 30 having the different degrees of hardness h in order.

Specifically, the hardness h of the bag 30 is compared between Stage 1 and Stage 2, for example, and evaluation is performed as to (1) which stage is hard (2) to what extent, using Levels 1 to 5, for example. This level evaluation is performed for combinations of Stages 1 to 7, i.e., a total of $_7C_2=21$ combinations.

Namely, the level evaluation is performed for respective combinations of Stage 1 and Stage 2, Stage 1 and Stage 3, . . . and Stage 1 and Stage 7, next, for respective combinations of Stage 2 and Stage 3, Stage 2 and Stage 4, . . . and Stage 2 and Stage 7, further for respective combinations of Stage 3 and Stage 4, . . . , Stage 4 and Stage 5, . . . , and Stage 5 and Stage 6, and finally for a combination of Stage 6 and Stage 7.

Here, the five levels are set as follows: (i) "the bag felt very hard in the first chewing", (ii) "the bag felt relatively hard in the first chewing", (iii) "the degree of hardness is substantially the same between the first chewing and the second chewing", (iv) "the bag felt relatively hard in the second chewing", and (v) "the bag felt very hard in the second chewing", and (i) to (v) are converted to scores (numerical values).

Specifically, as for the score of the stage of the first chewing, if (i) is selected, this is converted to "4", and if (ii) is selected, this is converted to "2". Similarly, (iii) is converted to "0", (iv) is converted to "−2", and (v) is converted to "−4". To the contrary, as for the score of the stage of the second chewing, if (i) is selected, this is converted to "−4", and if (ii) is selected, this is converted to "−2". Similarly, (iii) is converted to "0", (iv) is converted to "2", and (v) is converted to "4". Namely, if a stage is felt hard relative to a compared stage, the score of the stage is increased.

As described above, an evaluated level of the hardness of each stage relative to a compared stage is converted to a score. This conversion to a score is performed with respect to evaluation of the above-described 21 combinations.

An average value of scores of a stage is plotted as a relative score of the stage. Plotted results will be described later with reference to FIG. 5.

2. Experiment Method

In this experiment, the user 60 practices the following procedure (2-1) to (2-4) once, and after the practice, performs the procedure (2-1) to (2-4) with respect to the above-described 21 combinations.

(2-1) First, while the hardness h of the bag 30 is maintained using the vacuum pump 20, the bag 30 is chewed for 10 seconds such that the following conditions (a) to (c) are satisfied (this will be referred to as the "first chewing").
Specifically,
(a) chew the bag between front teeth and back teeth on the right side as viewed from the user 60,
(b) chew the vicinity of a center portion of the bag 30, and
(c) chew the bag in a usual manner as if when having a meal.
(2-2) After ceasing chewing, the user waits for 10 seconds. While waiting, the user uniformly spreads the content of the bag.
(2-3) The bag 30 is chewed again for 10 seconds such that the above-described conditions (a) to (c) are satisfied (this will be referred to as the "second chewing").
(2-4) After ceasing chewing, level evaluation is performed by k (k: natural number) subjects by evaluating in which of the first chewing (2-1) and the second chewing (2-3), the bag felt harder, using the levels (i) to (v).

3. Experiment Result

Figure 5:
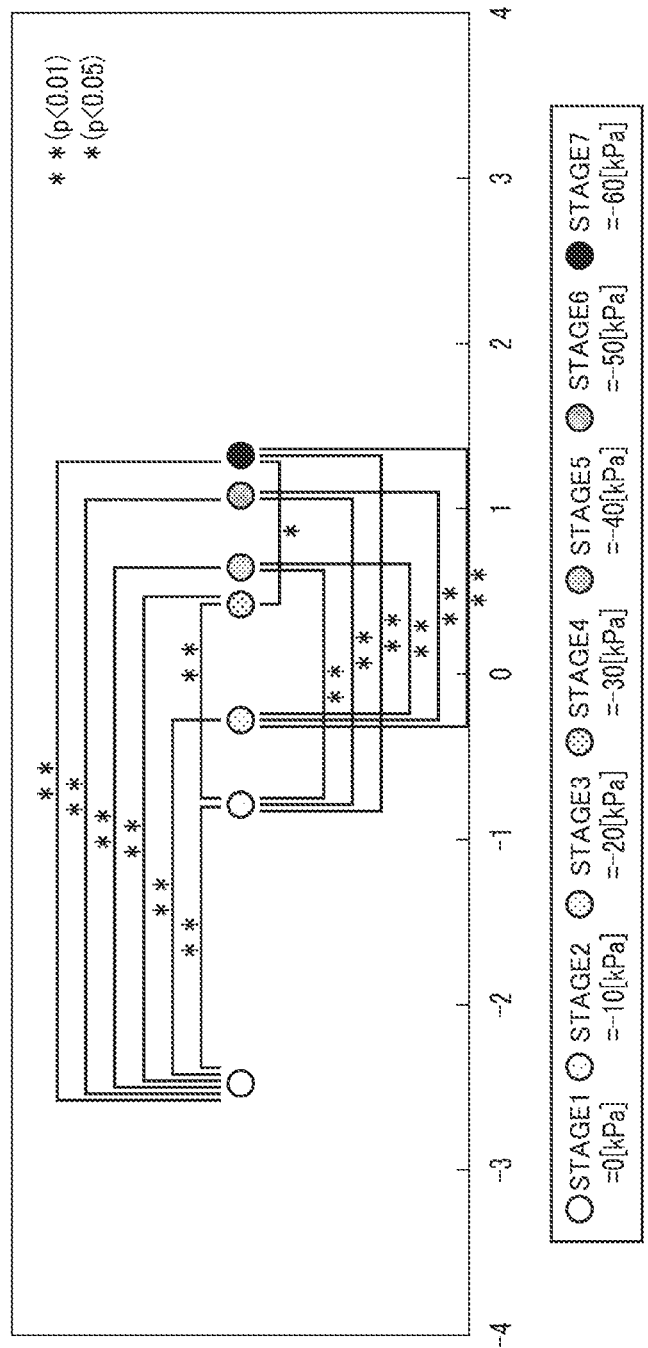
FIG. 5 is a diagram showing results of sensory evaluation of hardness of respective stages that are plotted in accordance with the Scheffe's method of paired comparisons to create a database to be recorded in a hardness/air pressure correspondence recording unit that is provided in the mock food texture presenting apparatus shown in FIG. 1.

FIG. 5 shows the result of the experiment.

FIG. 5 is a diagram (graph) showing results of sensory evaluation of the respective stages plotted in accordance with the Scheffé's method of paired comparisons. Sensory evaluation means evaluation of properties of a target (in this example, the hardness h of the bag 30) performed using senses of a user.

First, how to read measurement data shown in the graph will be described.

Relative scores of the respective stages are plotted on a horizontal axis (psychological scale of the hardness) of the graph. These scores are results of the level evaluation of relative hardness performed by the k subjects for the above-described 21 combinations, and accordingly the scores of the respective stages are plotted as relative scores on the psychological scale of the hardness. The horizontal axis of the graph represents the psychological scale of the hardness, and 4 is the relative score for a case in which the bag felt hardest and −4 is the relative score for a case in which the bag felt softest.

Namely, when Stage 1 is viewed from Stage 2, for example, the k subjects felt Stage 1 very soft, and consequently Stage 1 has a difference of about "−1.7" from Stage 2 on the psychological scale.

In contrast, if the hardness h of the bag 30 is increased to Stages 5, 6, and 7, for example, the bag having the hardness h of Stages 5, 6, and 7 can be recognized as having a different degree of hardness h from Stage 2. However, the subjects did not feel much difference in hardness h between Stages 5, 6, and 7, and consequently the difference between Stage 5 and Stage 6 on the psychological scale is about "0.4". The difference between Stage 6 and Stage 7 is as small as about "0.2".

When the hardness h of Stage 1 is viewed from Stage 7, for example, the hardness h of Stage 1 felt considerably soft compared to when the bag 30 having the hardness h of Stage 7 was chewed, and consequently the difference between Stage 1 and Stage 7 on the psychological scale is about "−3.8".

Here, solid lines are shown between the stages, and "*" and "**" are shown above or under the solid lines. These solid lines, "*", and "**" indicate that there is a "predetermined significant difference" between two stages (for example, Stage 1 and Stage 2).

A "significant difference" means a "meaningful difference", rather than a difference that is generated accidentally or due to an error.

For example, Stage 1 and Stage 2 are connected to each other by a solid line with "** ($p<0.01$)".

Further, for example, Stage 4 and Stage 7 are connected to each other by a solid line with "* ($p<0.05$)".

Here, p represents a p value, which is an index for determining whether or not there is a significant difference, and if the p value is smaller than a significance level (usually 5%), it is determined that there is a significant difference.

The significance level is a probability that serves as a reference when determining that the occurrence of a phenomenon is unlikely to be an accident based on the probability of the occurrence (i.e., the probability of the occurrence is significant).

Namely, if the p value that is obtained when a phenomenon (for example, in evaluation of Stage 1 and Stage 2, a result (i) "the bag felt very hard in the first chewing") occurs is 5% or less, it is determined that a measurement result obtained in the phenomenon is unlikely to be accidentally obtained and the phenomenon occurs with a probability of 95% or more, namely, there is a significant difference.

In this experiment, in the level evaluation performed for combinations of Stage 1 and Stages 2 to 7, Stage 2 and Stages 4 to 7, and Stage 3 and Stages 5 to 7, the p value=0.01 or less (<significance level=1%) is obtained, and accordingly it is found that the user 60 can sense a hardness difference with a probability of 99% or more in their mouth.

Note that, in the evaluation performed for a combination of Stage 4 and Stage 7, $0.01<p$ value$<0.05$ is obtained, and accordingly it is found that the user 60 can sense a hardness difference with a probability of 95% or more in their mouth.

As described above, in this experiment, it is determined that the user 60 can sense a difference in hardness h (i.e., there is a significant difference) between Stage 1 and Stages 2 to 7, Stage 2 and Stages 4 to 7, Stage 3 and Stages 5 to 7, and Stage 4 and Stage 7.

Next, a method (1. conditions, 2. result) for creating a database for the hardness/air pressure correspondence recording unit 13g based on the result (FIG. 5) obtained in the above-described preliminary process will be described. If this database is created, it is possible to obtain a relationship between a combination of stages between which the user 60 can recognize a hardness difference most frequently when chewing and air pressures [kPa] that are required to present the respective stages.

1. Conditions

Out of the stages (Stages 1 to 7), a combination of stages between which the user 60 can sense a hardness difference most frequently in a process of increasing the number n of times of chewing is determined. Specifically, a combination of stages with which the largest number of hardness differences can be obtained when the hardness h is reduced/increased from each stage and air pressures [kPa] that are required to achieve the hardness h of the combined stages are determined by considering the significant difference.

Here, assume that, as the number n of times of chewing is increased, the hardness h of the bag 30 is increased/reduced based on a database that is recorded in the chewing number of times/hardness correspondence recording unit 13f and in which the number n of times of chewing is associated with the hardness h of the bag 30, and the air pressure is increased/reduced to be an air pressure [kPa] that is required to achieve the hardness h.

2. Result

The following describes one example of an inappropriate combination for the sake of understanding of the creation of the database. The following example is an example of a case in which a different degree of hardness is presented every time the bag is chewed.

As shown in FIG. 5, if the bag 30 having the hardness h of Stage 2 is chewed first and the hardness h is reduced, for example, chewing ends with the hardness h of Stage 1, which is closest to Stage 2 out of stages that have a significant difference from Stage 2. Namely, the user 60 ends chewing when the number n of times of chewing is 2.

Conversely, the hardness h of the bag 30 is increased from Stage 2. In this case, if the user 60 has chewed the bag 30 of Stage 2 and the number n of times of chewing is then increased by one, for example, the stage of hardness h that is closest to Stage 2 out of stages for which the user 60 can sense a change of the hardness h of the bag 30 is Stage 4.

This is because Stage 2 and Stage 3 are not connected to each other by a solid line, and therefore "there is not a significant difference" therebetween and it is considered that the user 60 cannot sense a change from Stage 2 to Stage 3 when the number n of times of chewing is increased.

According to a similar way of thinking, if the number n of times of chewing is further increased by one, the stage of hardness that is closest to Stage 4 out of stages for which the user can sense a change of the hardness h of the bag 30 is Stage 7.

Namely, the user 60 ends chewing when the number n of times of chewing is 3. This number n of times of chewing obtained when chewing is started from Stage 2 is small compared to a value that is obtained with an optimal combination (pattern that starts from Stage 7 (or Stage 1)) described below.

Namely, according to the above-described way of thinking, in a process of increasing the number n of times of chewing one by one, the number of combinations of stages is the largest if the user 60 first chews the bag 30 having the hardness h of the highest Stage 7 (or the lowest Stage 1).

Namely, if chewing is started from. Stage 7, the stage of hardness h that is closest to Stage 7 out of stages for which a change of the hardness h of the bag 30 can be sensed next is Stage 4.

When the number n of times of chewing is further increased by one, the stage of hardness that is closest to Stage 4 out of stages for which a change of the hardness h of the bag 30 can be sensed is Stage 2, and when the number n of times of chewing is finally increased by one, the stage of hardness that is closest to Stage 2 out of stages for which a change of the hardness h of the bag 30 can be sensed is Stage 1.

Accordingly, the number n of times of chewing performed by the user 60 is "4", which is the largest value. In this example, it is assumed that the hardness is varied according to the stage of chewing every time the bag is chewed, but the hardness may also be varied according to the stage of chewing after the bag is chewed a predetermined number of times, without changing the number of stages of chewing.

A combination of these stages (Stage 1, Stage 2, Stage 4, and Stage 7) is recorded together with corresponding air pressures [kPa] in the hardness/air pressure correspondence recording unit 13g.

FIG. 6 is a database that is recorded in the hardness/air pressure correspondence recording unit 13g and shows a relationship between the combination of stages between which the user 60 can recognize a hardness difference most frequently and air pressures [kPa] that are required to present the respective stages, based on FIG. 5.

In FIG. 6, stages that can be sensed by the user 60 when the number n of times of chewing is increased are numbered, and air pressures [kPa] that are required to achieve the hardness h of these stages are shown.

It can be found that, if chewing is started from Stage 7 (Stage 1), the user 60 can sense a hardness difference between four stages (Stage 1, Stage 2, Stage 4, and Stage 7) at most.

Next, a method (1. procedure, 2. result) for creating a database for the air pressure/duty ratio correspondence recording unit 13h will be described.

1. Procedure (1) The duty ratio is varied from 0 [%] to 100 [%] (always ON).

(2) After two seconds have elapsed from when the duty ratio is specified, the air pressure [kPa] inside the bag 30 is acquired a total of 100 times for every 10 [ms].

(3) An average value of the air pressure [kPa] inside the bag 30 acquired 100 times is calculated.

2. Result

Figure 7:
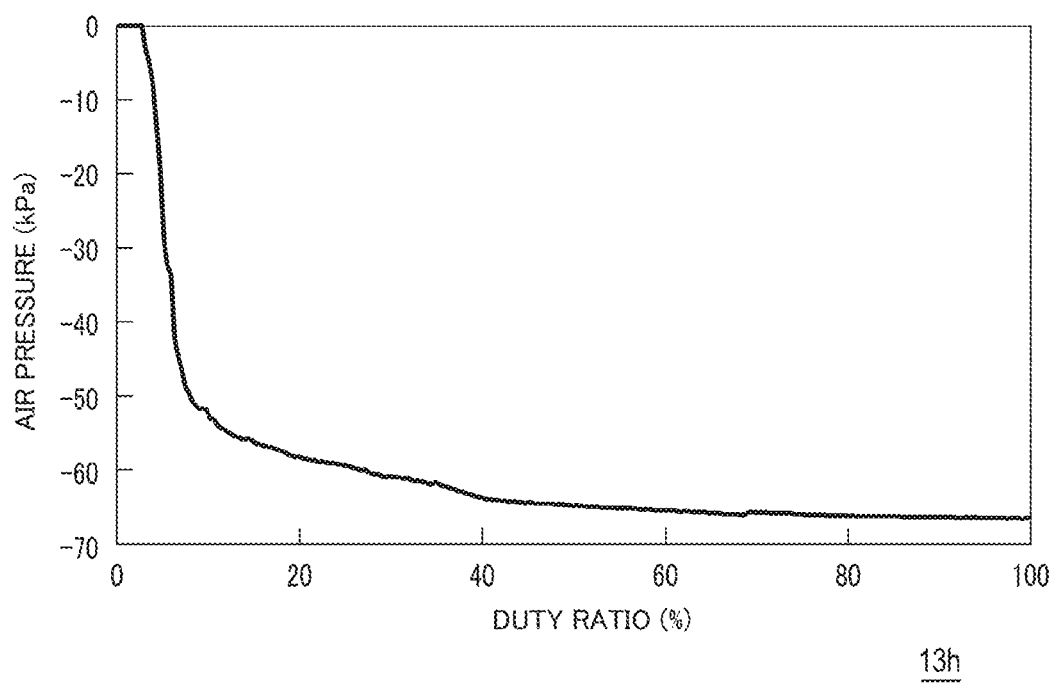
FIG. 7 is a database that shows a relationship between an air pressure inside a bag and a duty ratio that is set for a vacuum pump provided in the mock food texture presenting apparatus shown in FIG. 1.

FIG. 7 shows a database that is recorded in the air pressure/duty ratio correspondence recording unit 13h. The database shown in FIG. 7 shows a relationship between the duty ratio [%] of a PWM signal that is set for the vacuum pump 20 and the air pressure [kPa].

If the duty ratio is increased up to approximately 100 [%], the vacuum pump 20 is always turned ON, and accordingly the air pressure [kPa] inside the bag 30 is reduced.

Through the above, processes for creating respective databases (the threshold value recording unit 13e, the hardness/air pressure correspondence recording unit 13g, and the air pressure/duty ratio correspondence recording unit 13h) are completed.

Mock Food Texture Presenting Process

Next, a mock food texture presenting process that is performed by the mock food texture presenting apparatus 1 according to the present embodiment will be described.

Figure 8:
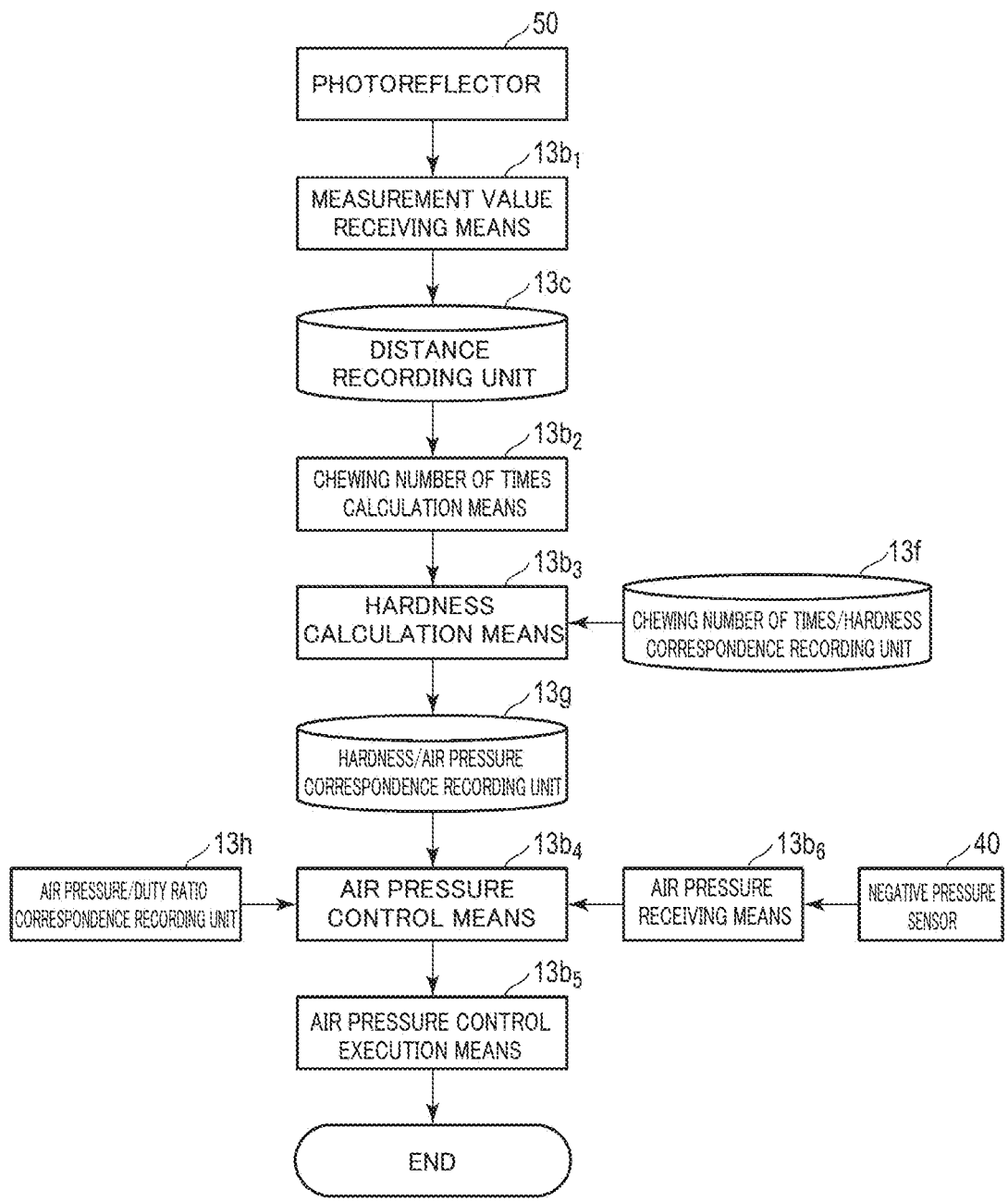
FIG. 8 is a block diagram showing a mock food texture presenting process realized by the mock food texture presenting apparatus shown in FIG. 1.

FIG. 8 is a block diagram showing the mock food texture presenting process that is realized as a result of the CPU 11 of the mock food texture presenting apparatus 1 executing the mock food texture presenting process program 13b using the work area 12a.

Namely, the CPU 11 functions as measurement value receiving means $13b_1$, chewing number of times calculation means (chewing number of times measurement means) $13b_2$, hardness calculation means $13b_3$, air pressure control means $13b_4$, and air pressure control execution means $13b_5$, following the mock food texture presenting process program 13b. Note that air pressure receiving means $13b_6$ will be described later.

The measurement value receiving means $13b_1$ has a function of receiving the distance l between the photoreflector 50 and the lower jaw lj of the user 60, which is measured by the photoreflector 50, together with a time t, and recording the received distance l and time t in the distance recording unit 13c.

The chewing number of times calculation means $13b_2$ has a function of counting the number n of times of chewing performed by the user 60. Specifically, the chewing number of times calculation means $13b_2$ compares the time t and the distance l recorded in the distance recording unit 13c with the threshold value lth recorded in the threshold value recording unit 13e, and upon determining that, for example, (1) the distance l at the time t is larger than the threshold value lth and (2) the distance l at a time t+1 is smaller than the threshold value lth, supposes that the mouth is transitioning from a closed state after the completion of chewing to an open state, and increases the number n of times of chewing by one.

Figure 9:
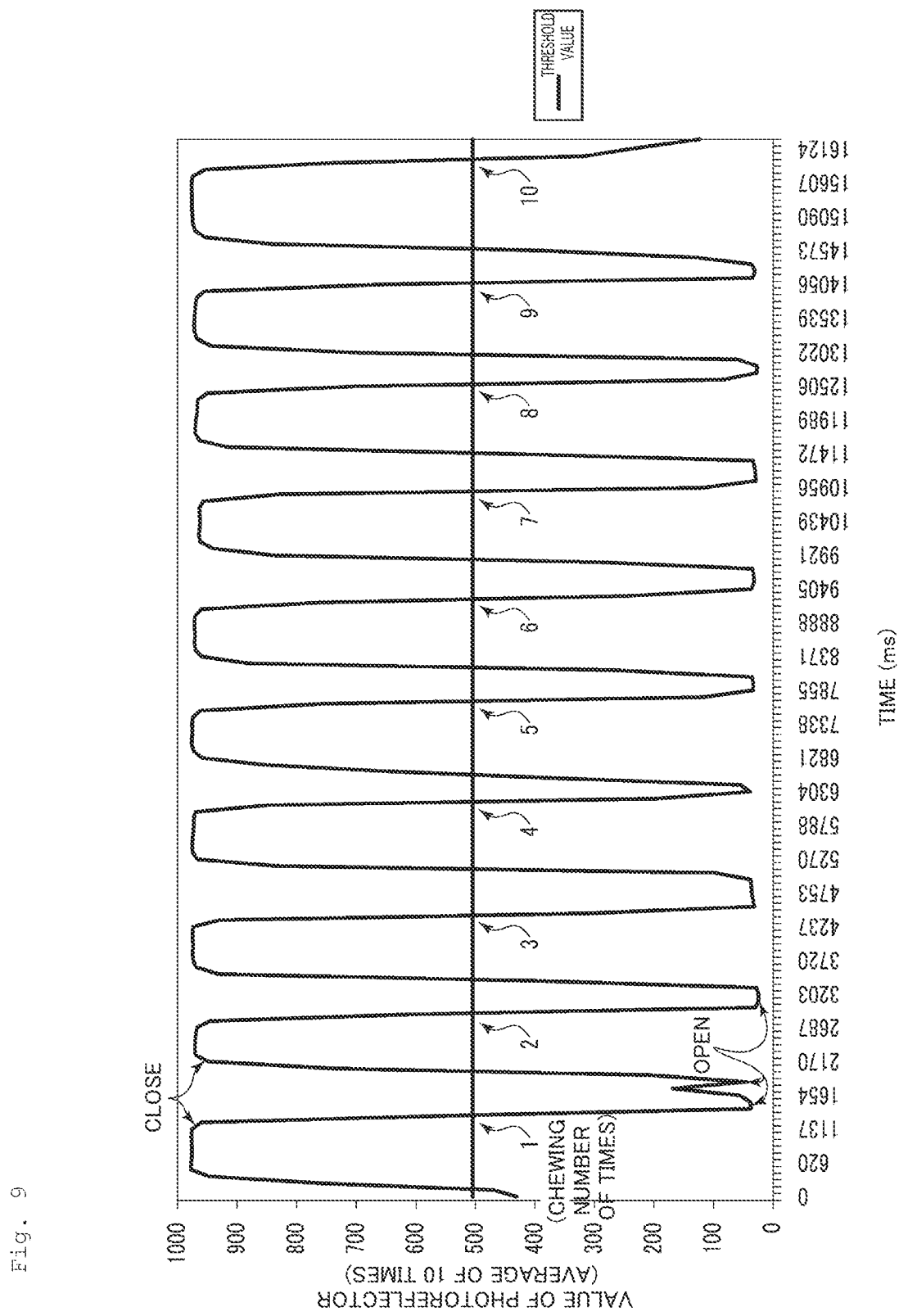
FIG. 9 is a diagram showing a state in which the number of times of chewing is counted depending on a distance measured using the photoreflector provided in the mock food texture presenting apparatus shown in FIG. 1.
Figure 10A:
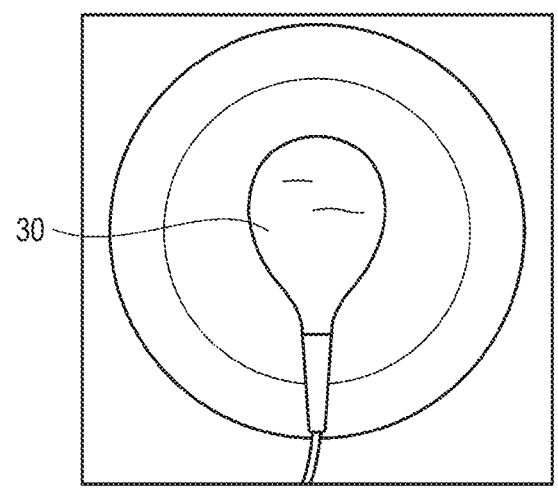
FIG. 10A is a diagram showing a state in which the inside of a bag is adjusted to 0 [kPa] by performing sucking using the vacuum pump provided in the mock food texture presenting apparatus shown in FIG. 1.
Figure 10B:
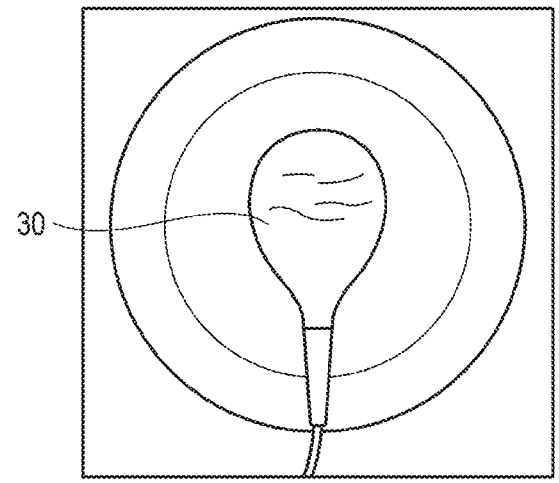
FIG. 10B is a diagram showing a state in which the inside of the bag is adjusted to −10 [kPa] by performing sucking using the vacuum pump provided in the mock food texture presenting apparatus shown in FIG. 1.
Figure 10C:
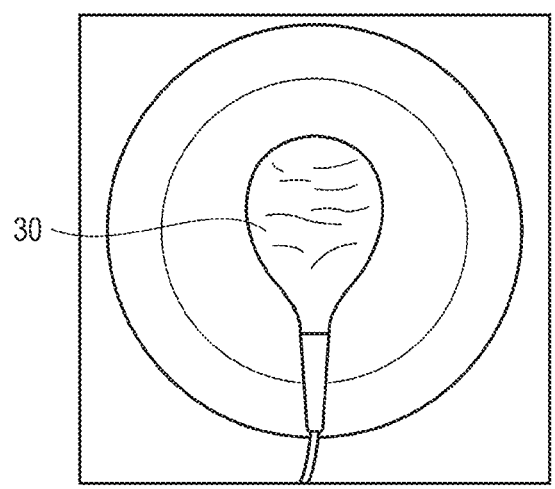
FIG. 10C is a diagram showing a state in which the inside of the bag is adjusted to −30 [kPa] by performing sucking using the vacuum pump provided in the mock food texture presenting apparatus shown in FIG. 1.
Figure 10D:
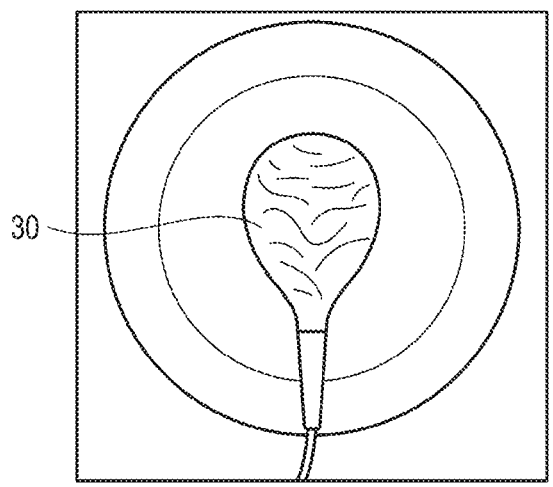
FIG. 10D is a diagram showing a state in which the inside of the bag is adjusted to −60 [kPa] by performing sucking using the vacuum pump provided in the mock food texture presenting apparatus shown in FIG. 1.

FIG. 9 is a diagram showing a state in which the number n of times of chewing is counted by determining whether the distance l measured together with the time t using the photoreflector 50 is larger or smaller than the threshold value lth recorded in the threshold value recording unit 13e.

Here, assume that the threshold value lth recorded in the threshold value recording unit 13e is 505. When t=1137 [ms] for example, the distance l is larger than the threshold value lth, and when t+1=1654 [ms], the distance l is smaller than the threshold value lth.

Therefore, the chewing number of times calculation means $13b_2$ detects a change in the distance l and increases the number n of times of chewing by one. With use of such means, the number n of times of chewing can be accurately counted. Thereafter, a similar process is repeated (a total of 10 times in FIG. 9). The number n of times of chewing may also be calculated using another method, such as individually determining and counting the closed state and the open state of the mouth.

Next, a function of the hardness calculation means $13b_3$ will be described. Based on the database that is recorded in the chewing number of times/hardness correspondence recording unit 13f and in which the number n of times of chewing is associated with the hardness h of the bag 30, the hardness calculation means $13b_3$ calculates the hardness h of the bag 30 according to the number n of times of chewing calculated by the chewing number of times calculation means $13b_2$.

The air pressure control means $13b_4$ first extracts, from the database recorded in the hardness/air pressure correspondence recording unit 13g, an air pressure [kPa] that is required to achieve the hardness h of the bag 30 that the hardness calculation means $13b_3$ calculated based on the number n of times of chewing calculated by the chewing number of times calculation means $13b_2$. Next, the air pressure control means $13b_4$ sets the duty ratio of a PWM signal according to the required air pressure [kPa], by referring to the air pressure/duty ratio correspondence recording unit 13h based on the extracted air pressure [kPa] required to achieve the hardness h.

Note that the air pressure control means $13b_4$ functions as hardness extraction means when extracting the hardness h from the database recorded in the hardness/air pressure correspondence recording unit 13g.

Finally, the air pressure control execution means $13b_5$ adjusts (controls) the air pressure [kPa] inside the bag 30 by controlling the number of revolution of the motor of the vacuum pump 20 based on the duty ratio supplied from the air pressure control means $13b_4$.

Namely, if it is determined that the number n of times of chewing is increased, the duty ratio set for the vacuum pump 20 is reduced to reduce the hardness h of the bag 30 from Stage 7 to Stage 4, Stage 2, and Stage 1 in this order along with the increase of the number n of times of chewing, and thus a change in the hardness that is similar to food texture felt when a food is actually chewed can be presented.

Note that the CPU 11 may also function as the air pressure receiving means $13b_6$ following the mock food texture presenting process program 13b. In this case, a configuration is also possible in which the air pressure [kPa] inside the bag 30 is received from the negative pressure sensor 40 using the air pressure receiving means $13b_6$, and the received air pressure [kPa] is controlled while measured to approach a value that is required to achieve the hardness h.

According to the mock food texture presenting apparatus 1, the number n of times of chewing is counted by the chewing number of times calculation means $13b_2$ based on a change in the distance l from the photoreflector 50, which is received by the measurement value receiving means $13b_1$ together with the time t. Then, to vary the hardness h of the bag 30 to a stage that can be sensed, according to the number n of times of chewing, a required air pressure is set according to the current number n of times of chewing based on the hardness/air pressure correspondence recording unit 13g in which stages that have a significant difference from each other and are stored in association with the number n of times of chewing are recorded. To realize the set air pressure inside the bag 30, the amount of sucking performed using the vacuum pump 20 is controlled in accordance with the air pressure control means $13b_4$.

Thus, different textures (degrees of hardness h) of the bag 30 can be presented to the user 60 through the jamming transition that occurs inside the bag 30 as a result of the air pressure inside the bag 30 being controlled according to conditions of chewing performed by the user 60. In the above-described example, a change in the distance to the lower jaw in the up-down direction is measured using the photoreflector 50, but a configuration is also possible in which the photoreflector is arranged such that a change in a distance in the front-back direction and/or the left-right direction can be measured to detect the number of times and the strength of chewing, such as grinding, and a change in the hardness h corresponding to chewing, such as grinding, is defined and used to present food texture.

Note that the shape of the bag 30 shown in the present embodiment is not limited to one shape. Namely, a configuration is also possible in which the bag 30 has a shape other than that shown in FIG. 1, e.g., the bag 30 is deformed into a different shape, such as a rectangular parallelepiped shape, and different degrees of hardness of the rectangular parallelepiped bag 30 are presented through the jamming transition by controlling the density of the powder or granular material according to conditions of chewing performed by the user 60.

FIGS. 10A to 10D show states in which the air pressure [kPa] inside the bag 30 shown in FIG. 1 is controlled using the vacuum pump 20.

FIGS. 10A to 10D are diagrams showing states in which the air pressure [kPa] inside the bag 30 is varied from 0 [kPa] (hardness is Stage 1) to −10 [kPa] (Stage 2), −30 [kPa] (Stage 4), and −60 [kPa] (Stage 7) by performing sucking using the vacuum pump 20 while maintaining substantially the same shape.

By controlling the air pressure [kPa] inside the bag 30 using the vacuum pump 20, the hardness h of the bag 30 can be set to any of Stage 1, Stage 2, Stage 4, and Stage 7 between which the user 60 can recognize a hardness difference.

If the air pressure [kPa] inside the bag 30 (the stage of hardness) is varied as described above according to the number n of times of chewing, the user 60 can sense different degrees of hardness h of the bag 30 maintaining substantially the same shape.

Next, FIGS. 11A to 11D show states in which different food textures (degrees of hardness h) are presented by deforming the bag 30 into a shape different from that shown in FIG. 1. First, the air pressure inside the bag 30 is set to 0 [kPa] (see FIG. 11A), and the bag 30 is deformed in this state (see FIG. 11B).

Figure 11A:
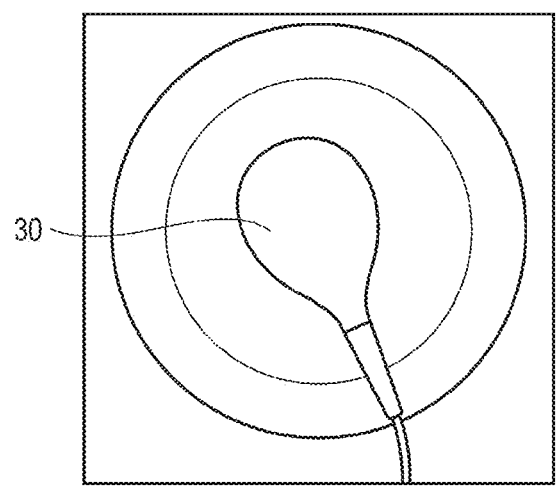
FIG. 11A is a diagram showing a state in which control of the air pressure performed using the vacuum pump shown in FIG. 1 is ceased before the shape of a bag is changed.
Figure 11B:
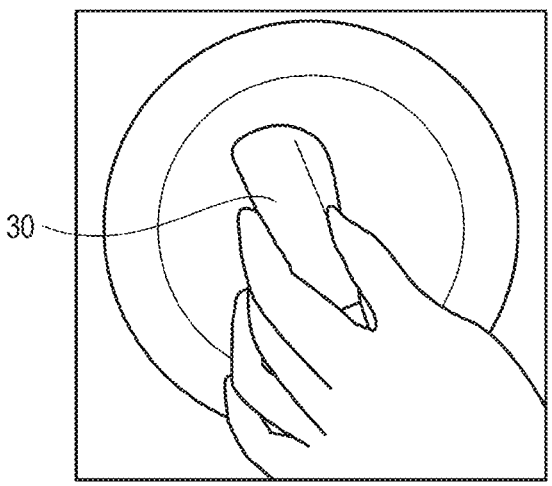
FIG. 11B is a diagram showing a state in which the bag shown in FIG. 1 is deformed into a different shape.
Figure 11C:
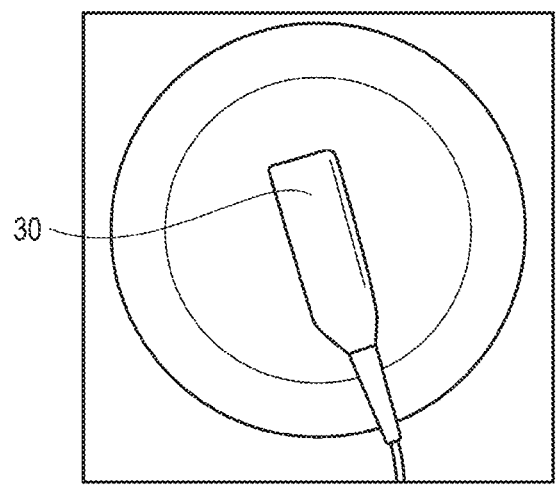
FIG. 11C is a diagram showing a state in which, after the bag is deformed into the different shape, the bag is presented while the deformed shape is maintained by controlling the air pressure using the vacuum pump.
Figure 11D:
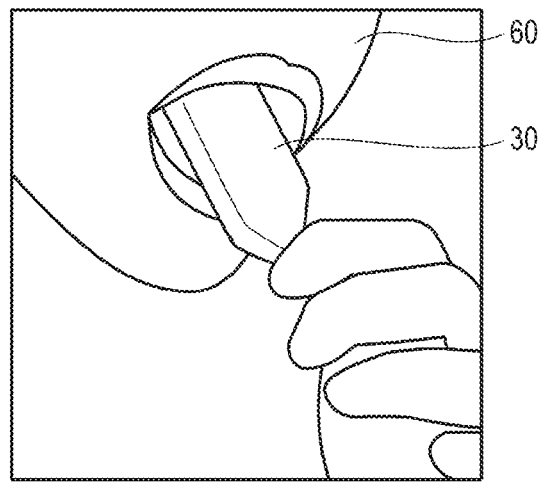
FIG. 11D is a diagram showing a state in which the bag deformed into the different shape is presented in the mouth of a user.

Thereafter, while maintaining the shape of the bag 30 by setting the air pressure inside the bag 30 to −5 [kPa] (see FIG. 11C), the bag 30 is presented to the user 60 (see FIG. 11D). In other words, a different shape of the bag 30 is presented to the user 60 with the density of the powder or granular material enclosed in the bag 30 fixed.

Then, the hardness h of the bag 30 is set to three stages (−10 [kPa], −30 [kPa], and −60 [kPa]), for example, by controlling the air pressure [kPa] inside the bag 30 by performing sucking using the vacuum pump 20 in accordance with the hardness/air pressure correspondence recording unit 13g.

Different degrees of hardness h that can be sensed by the user 60 can be presented in the case of the bag 30 having a different shape as well.

In the above-described example, the enclosing body is constituted by the single bag 30. However, the enclosing body may also be constituted by a plurality of bags. A configuration is also possible in which the enclosing body has a structure (first structure) in which a plurality of bags are arranged side by side e.g., arranged next to each other like the segments of an orange, or a multi-layer structure (second structure) that is constituted by an outer skin (bag) that covers the outer side of the enclosing body and an inner skin (bag) that is entirely covered by the outer skin on the outer side like a fondant chocolate. In this case, it is also possible to present different food textures to the user 60 by varying the hardness h for each bag.

Furthermore, the enclosing body may also have a structure (third structure) that is a combination of the first structure and the second structure. For example, the enclosing body may also have a structure as if the segments of an orange are arranged next to each other inside a fondant chocolate.

Note that a powder or granular material such as coffee powder is enclosed in the bag 30 in the mock food texture presenting apparatus 1, but there is no limitation thereto, and a smooth powder or granular material, such as dogtooth violet starch, may also be enclosed in the bag 30.

If the enclosing body is constituted by a plurality of bags, it is also possible to employ a configuration in which a powder or granular material enclosed in at least one bag of the plurality of bags differs from a powder or granular material enclosed in another bag of the plurality of bags. For example, a configuration is also possible in which the powder or granular material is changed for every bag, such as enclosing coffee powder in one bag and enclosing dogtooth violet starch in another bag.

Furthermore, the material of the bag 30 is not limited to rubber, and may also be changed to a flexible material such as silicone.

If the enclosing body is constituted by a plurality of bags, it is also possible to employ a configuration in which the material of at least one bag of the plurality of bags differs from the material of another bag of the plurality of bags.

Furthermore, it is also possible to divide the bag 30 into a plurality of sections, cause the user 60 to chew the sections at different positions in their mouth, and individually control the hardness h of the sections (there may be a section for which the hardness h is not controlled) to present different degrees of hardness h depending on the position in the mouth.

Furthermore, the mock food texture presenting apparatus 1 may additionally have a density measuring function (density sensor) that can measure (calculate) the density of the powder or granular material enclosed in the bag 30. The density measuring function can measure the density of the powder or granular material by, for example, acquiring an initial volume of the powder or granular material in the bag, the volume (capacity) of the bag 30, and the amount of air remaining in the bag 30, in advance, and then measuring the volume (quantity) of air introduced into or discharged from the bag 30.

Note that, if the powder or granular material is sucked or discharged during measurement of the density, the density of the powder or granular material can also be measured by considering the varied volume of the powder or granular material in the bag and the amount of air that remains in the bag 30 when the volume of the powder or granular material is varied.

In this case, the hardness h of the bag 30 can be calculated from the measured density of the powder or granular material.

Also, the amount of air sucked from the bag 30 per unit time can be increased by increasing the rate of reaction of the vacuum pump 20. In other words, a change amount of the air pressure [kPa] inside the bag 30 per unit time can be increased.

In this case, a database can be created in the chewing number of times/hardness correspondence recording unit 13f such that the change amount of the air pressure [kPa] inside the bag 30 per unit time is rapidly varied at the moment when the number n of times of chewing is changed to one (i.e., the bag is chewed for the first time), e.g., the hardness h of the bag 30 in Stage 7 (−60 [kPa]) is rapidly varied to the hardness h of Stage 1 (0 [kPa]).

If food texture is to be varied instantaneously as described above, the air pressure inside the bag 30 is varied to 0 [kPa] using the vacuum pump 20 at the moment when the bag is chewed, and the density of the powder or granular material enclosed in the bag 30 or the volume (capacity) of the bag 30 is varied to a value with which the shape of the bag 30 cannot be maintained, for example.

Thus, the mock food texture presenting apparatus 1 can present food texture of a food, such as a rice cracker, that instantaneously varies when chewed.

Furthermore, although the hardness h of the bag 30 is discretely varied (in the order of Stage 7, Stage 4, Stage 2, and Stage 1) according to the number n of times of chewing, a configuration is also possible in which the hardness h is continuously varied, rather than discretely. In this case, it is possible to present food texture by continuously and smoothly varying the hardness h of the bag 30.

In the above-described example, the density of the powder or granular material in the bag 30 is varied by controlling the air pressure inside the bag 30 using the vacuum pump 20, but it is also possible to vary the density of the powder or granular material by providing a structure for sucking the powder or granular material into the bag 30 or discharging the powder or granular material from the bag 30 to increase or reduce the volume of the powder or granular material in the bag.

Furthermore, it is also possible to combine the use of the vacuum pump and sucking and discharging of the powder or granular material to increase or reduce the capacity (size) of the bag 30 and change its shape while maintaining the hardness h of the bag 30 (or the density of the powder or granular material), or to vary the hardness h while maintaining the shape of the bag 30.

Furthermore, a configuration is also possible in which a pressure sensor for measuring pressure applied to the bag 30 is provided inside the bag 30.

If this configuration is employed, the chewing number of times calculation means $13b_2$ can measure the number n of times of chewing based on a measurement value (for example, the strength of chewing performed on the bag 30 by the user 60 or the position of the bag 30 chewed by the user 60) measured using the pressure sensor.

For example, a person may vary the strength of chewing depending on the hardness of the chewed object, and therefore the number n of times of chewing according to the current hardness h of the bag 30 can be calculated based on the strength of chewing performed by the user 60, which is measured using the pressure sensor.

Namely, the current hardness h of the bag 30 can be estimated based on the currently measured strength of chewing, and therefore the number n of times of chewing that needs to be performed by the user 60 to reach the estimated hardness h can be calculated.

Alternatively, it is also possible to calculate, as the number n of times of chewing, the number of times measured strength of chewing has exceeded a threshold value, or calculate the number of times of chewing from an integrated value of measured strength of chewing by taking effects to the object into consideration.

Food texture and a change in the shape can be presented by calculating the hardness h of the bag 30 from the number n of times of chewing, the strength of chewing, and an integrated value of the strength of chewing, and controlling the density of the powder or granular material according to conditions of chewing actions of the user.

Furthermore, if the pressure sensor has a function of sensing the position to which pressure is applied, the chewing number of times calculation means $13b_2$ can measure the number of times pressure is applied (i.e., the number n of times of chewing) with respect to each position.

In this case, the hardness calculation means $13b_3$ can calculate the hardness h of the bag 30 to be presented, based on the number n of times of chewing measured by the chewing number of times calculation means $13b_2$.

Furthermore, a configuration is also possible in which the strength of chewing, a chewed position of the bag 30, and the number n of times of chewing are indirectly calculated (estimated) based on the state of the jaws of the user 60. For example, a configuration is also possible in which a pressure sensor is provided on a tissue, such as a jaw or a tooth, in the mouth of the user 60, rather than the bag 30, and the strength of chewing and the number n of times of chewing are measured by the chewing number of times calculation means $13b_2$.

Alternatively, the mock food texture presenting apparatus 1 may also have a configuration that includes at least one microphone (for example, bone conductive microphone) that can collect chewing sound generated by the user 60.

If this configuration is employed, the chewing number of times calculation means $13b_2$ can measure the strength of chewing, a chewed position of the bag 30, and the number n of times of chewing based on a source, volume, a change amount per unit time, etc., of the chewing sound that is generated as a result of the user 60 chewing the bag 30 and collected using the microphone.

Furthermore, the measurement value receiving means $13b_1$ may also have a function of receiving a change amount of the distance l per unit time from the photoreflector 50. In this case, if the change amount of the distance l per unit time is large, for example, it is possible to determine that the strength of chewing performed on the bag 30 by the user 60 is large.

The above-described first embodiment relates to a method for presenting food texture according to chewing movement of the mouth. Embodiments described below relate to methods for presenting food texture according to movement of the mouth different from chewing. Specifically, a method for presenting food texture according to licking movement of the mouth performed using the tongue will be described in a second embodiment, a method for presenting food texture according to rolling movement of the mouth performed in the mouth will be described in a third embodiment, and a method for presenting food texture according to sandwiching movement of the mouth performed using teeth, lips, the tongue, etc., or pressing movement of the mouth performed using the tongue will be described in a fourth embodiment. Note that descriptions of matter that is common between the first embodiment and the second to fourth embodiment are appropriately omitted.

Second Embodiment

Figure 12:
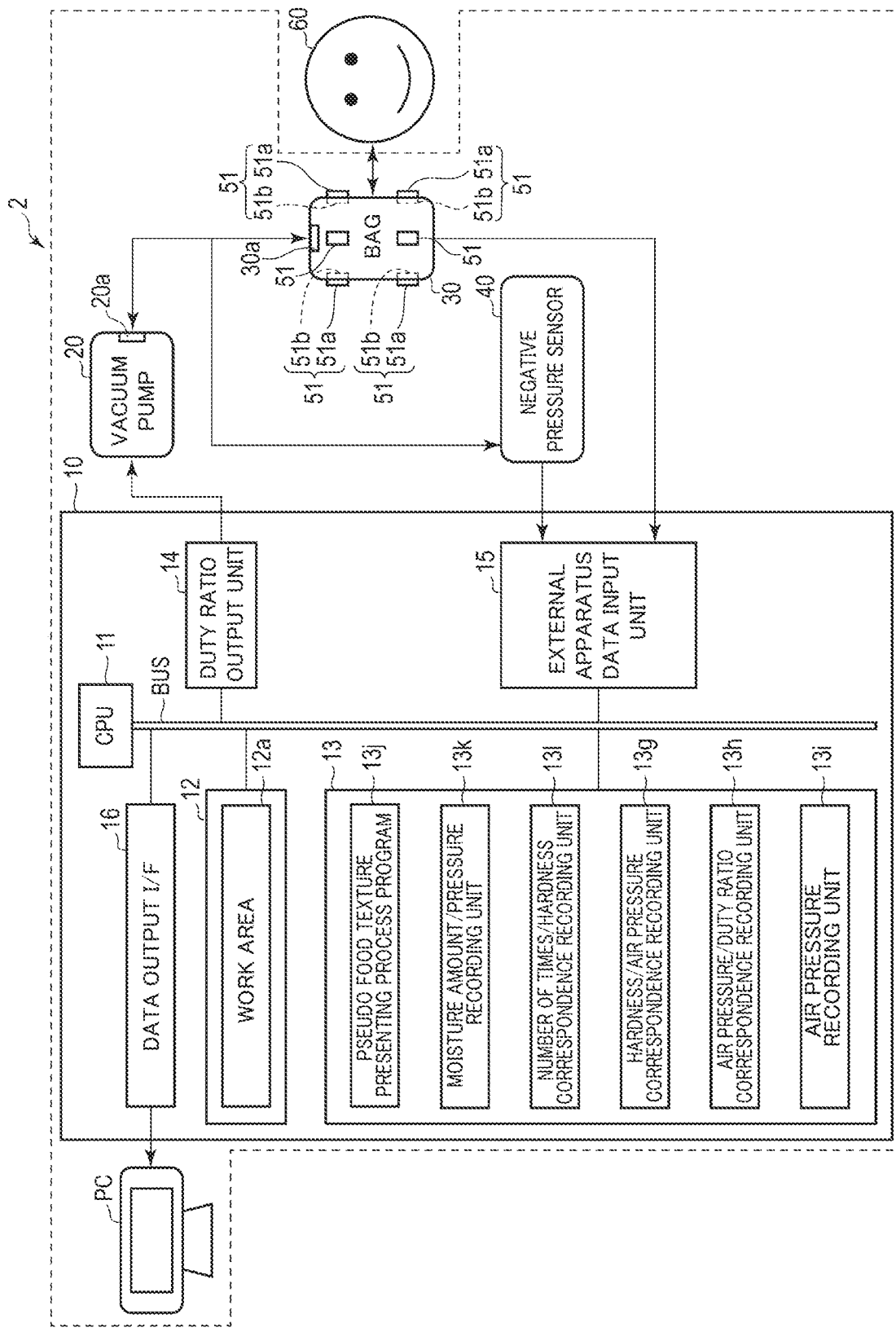
FIG. 12 is a block diagram showing a configuration of a mock food texture presenting apparatus according to a second embodiment.

FIG. 12 schematically shows a configuration of a mock food texture presenting apparatus 2 according to the second embodiment. As shown in FIG. 12, the mock food texture presenting apparatus 2 includes the microcomputer 10, the vacuum pump 20, the bag 30, the negative pressure sensor 40, a plurality of sensor pairs 51, and the personal computer PC. In FIG. 12, constitutional elements that are the same as the constitutional elements shown in FIG. 2 are denoted with the same reference signs as those shown in FIG. 2, and descriptions of these constitutional elements are omitted.

The plurality of sensor pairs 51 are respectively arranged at a plurality of positions (hereinafter may also be referred to as "sensor positions") on a surface of the bag 30. Each sensor pair 51 is a pair of a moisture sensor 51a and a pressure sensor 51b, and the moisture sensor 51a is arranged on an outer surface of the bag 30 and the pressure sensor 51b is arranged on an inner surface of the bag 30. Namely, in each sensor pair 51, the moisture sensor 51a is located opposite to the pressure sensor 51b via the surfaces of the bag 30. Here, the outer surface of the bag 30 is the surface on the outer side of the bag 30, and the inner surface of the bag 30 is the surface on the inner side of the bag 30. Specifically, the outer surface of the bag 30 comes into contact with tissues, such as teeth, the tongue, etc., in the mouth in a state in which the user 60 holds the bag 30 in their mouth, and the inner surface of the bag 30 defines an interior space in which the powder or granular material is enclosed.

The moisture sensor 51a measures the amount of moisture (amount of saliva) attached to a sensor position, and transmits, to the microcomputer 10, moisture amount data that includes a measurement value of the moisture amount and a measurement time that indicates a time at which the moisture amount is measured. Each moisture sensor 51a acquires measurement values at predetermined time intervals (for example, intervals of 10 milliseconds) and outputs moisture amount data in real time. The pressure sensor 51b measures pressure applied to a sensor position of the bag 30 from the outside, and transmits, to the microcomputer 10, pressure data that includes a measurement value of the pressure and a measurement time at which the pressure is measured. Each pressure sensor 51b acquires measurement values at predetermined time intervals (for example, intervals of 10 milliseconds) and outputs pressure data in real time.

The recording unit 13 in the microcomputer 10 includes a program area in which a mock food texture presenting process program 13j is stored, a moisture amount/pressure recording unit 13k, a number of times/hardness correspondence recording unit 13l, the hardness/air pressure correspondence recording unit 13g, the air pressure/duty ratio correspondence recording unit 13h, and the air pressure recording unit 13i.

The mock food texture presenting process program 13j is executed by the CPU 11 using the work area 12a. When executed by the CPU 11, the mock food texture presenting process program 13j causes the CPU 11 to perform a mock food texture presenting process, which will be described later.

The moisture amount/pressure recording unit 13k records measurement values of the moisture amount and the pressure acquired using the plurality of sensor pairs 51. In the moisture amount/pressure recording unit 13k, measurement values of the moisture amount and the pressure are recorded in association with measurement times and identification information for identifying the sensor pairs 51.

A correspondence table (database) in which the number of times the bag 30 has been licked with the tongue is associated with the hardness of the bag 30 is recorded in the number of times/hardness correspondence recording unit 13l in advance. The correspondence table is set such that, as the number of times the bag 30 has been licked with the tongue is increased, the hardness of the bag 30 is reduced, for example. A combination of stages between which a hardness difference can be sensed when the bag 30 is licked with the tongue can be identified by performing an experiment that is similar to the experiment described in the first embodiment. Assume that, through the experiment, a combination of Stage 7, Stage 3, and Stage 1 is identified as a combination of stages between which a hardness difference of the bag 30 can be sensed, for example. In this case, the hardness may be set to Stage 7 when the number of times is two or less, Stage 3 when the number of times is three, and Stage 1 when the number of times is four or more, for example. Even if the experiment result shows that a difference between the hardness of Stage 7 and the hardness of Stage 5 cannot be sensed, the hardness may be varied from Stage 7 to Stage 5. For example, the hardness may be set to Stage 7 when the number of times is one, Stage 5 when the number of times is two, Stage 3 when the number of times is three, and Stage 1 when the number of times is four or more.

Figure 13:
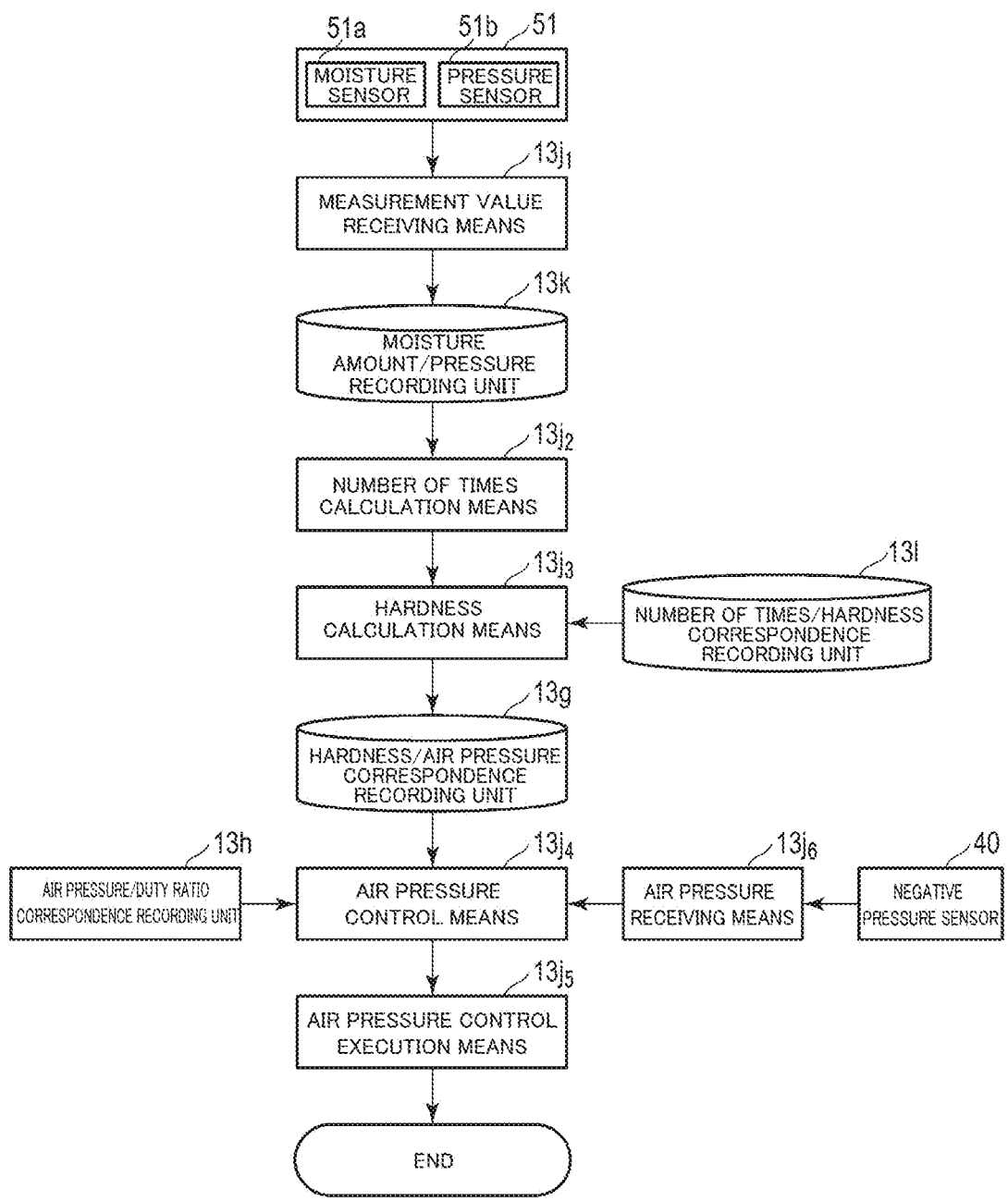
FIG. 13 is a block diagram showing a mock food texture presenting process realized by the mock food texture presenting apparatus shown in FIG. 12.

FIG. 13 schematically shows a mock food texture presenting process according to the present embodiment. The mock food texture presenting process shown in FIG. 13 is realized as a result of the CPU 11 in the microcomputer 10 executing the mock food texture presenting process program 13j. The CPU 11 functions as measurement value receiving means $13j_1$, number of times calculation means (number of times measurement means) $13j_2$, hardness calculation means $13j_3$, air pressure control means $13j_4$, and air pressure control execution means $13j_5$, following the mock food texture presenting process program 13j.

The measurement value receiving means $13j_1$ receives measurement data from the plurality of sensor pairs 51 via the external apparatus data input unit 15, and records the received measurement data in the moisture amount/pressure recording unit 13k. As described above, each sensor pair 51 includes a moisture sensor 51a and a pressure sensor 51b. The measurement value receiving means $13j_1$ receives moisture amount data from a plurality of moisture sensors 51a and receives pressure data from a plurality of pressure sensors 51b.

The number of times calculation means $13j_2$ calculates the number of times the user 60 has licked the bag 30 with their tongue, based on the measurement data received by the measurement value receiving means $13j_1$. For example, the number of times calculation means $13j_2$ calculates a feature value for each sensor pair 51 based on measurement values of the moisture amount and the pressure. When M represents a measurement value of the moisture amount and P represents a measurement value of the pressure, a feature value F is expressed as follows.

$$F = \alpha M + \beta P$$

Here, $\alpha$ and $\beta$ are parameters that are determined in advance.

The number of times calculation means $13j_2$ takes a sensor position that has the largest feature value to be a position that is licked by the user 60 with their tongue. The number of times calculation means $13j_2$ calculates the feature value at predetermined time intervals (for example, intervals of 10 milliseconds), and upon detecting a change of the sensor position having the largest feature value from a sensor position to another sensor position, recognizes that the position that is licked by the user 60 with their tongue is shifted. The number of times calculation means $13j_2$ counts the number of times the position licked by the user 60 with their tongue has shifted, as the number of times the user 60 has licked the bag 30 with their tongue.

Based on the correspondence table recorded in the number of times/hardness correspondence recording unit 13l, the hardness calculation means $13j_3$ calculates the hardness of the bag 30 according to the number of times calculated by the number of times calculation means $13j_2$. In the case of the above-described example, the hardness calculation means $13j_3$ determines the hardness as being Stage 7 when the measured number of times is two, and determines the hardness as being Stage 3 when the measured number of times thereafter changes to three.

The air pressure control means $13j_4$ and the air pressure control execution means $13j_5$ respectively perform the same processes as the above-described air pressure control means $13b_4$ and the air pressure control execution means $13b_5$ (FIG. 8). Therefore, descriptions of the air pressure control means $13j_4$ and the air pressure control execution means $13j_5$ are omitted.

Note that the CPU 11 may further function as air pressure receiving means $13j_6$ following the mock food texture presenting process program 13j. The air pressure receiving means $13j_6$ performs the same process as the above-described air pressure receiving means $13b_6$ (FIG. 8). Therefore, a description of the air pressure receiving means $13j_6$ is omitted.

Namely, the process for controlling the density of the powder or granular material in the bag 30 to realize the hardness calculated by the hardness calculation means $13j_3$ is common between the first embodiment and the second embodiment.

The mock food texture presenting apparatus 2 measures the number of times the user 60 has licked the bag 30 with their tongue, and controls the density of the powder or granular material based on the measured number of times such that the bag 30 has a degree of hardness according to the measured number of times. The correspondence table recorded in the number of times/hardness correspondence recording unit 13l may be set such that, as the number of times the user has licked the bag 30 with their tongue is increased, the hardness of the bag 30 is reduced, for example. In this case, it is possible to present texture of a food the entirety of which continuously becomes soft as licked with the tongue, for example.

In the above-described example, the moisture sensor 51a and the pressure sensor 51b are provided. However, a configuration is also possible in which only one of the moisture sensor 51a and the pressure sensor 51b is provided, or the moisture sensor 51a and the pressure sensor 51b are provided independently from each other, rather than as a pair. For example, a configuration is also possible in which a plurality of pressure sensors 51b are provided on the bag 30 (without providing the moisture sensors 51a), and the number of times the bag 30 has been licked with the tongue is calculated based on pressure data output from the pressure sensors 51b. It is also possible to use a sensor of a different type from the moisture sensor 51a and the pressure sensor 51b.

In the above-described example, the enclosing body is constituted by the single bag 30. Alternatively, the enclosing body may also be constituted by a plurality of bags 30. The enclosing body may have any one of the above-described first structure, second structure, and third structure.

If the enclosing body has the first structure, for example, a plurality of sensor pairs 51 are arranged in each of the plurality of bags 30. The CPU 11 calculates the number of times the user 60 has licked with the tongue with respect to each bag 30, and controls the hardness of each bag 30 based on a calculation result. In this case, it is possible to present texture of a food in which only a licked position becomes soft, for example.

Third Embodiment

Figure 14:
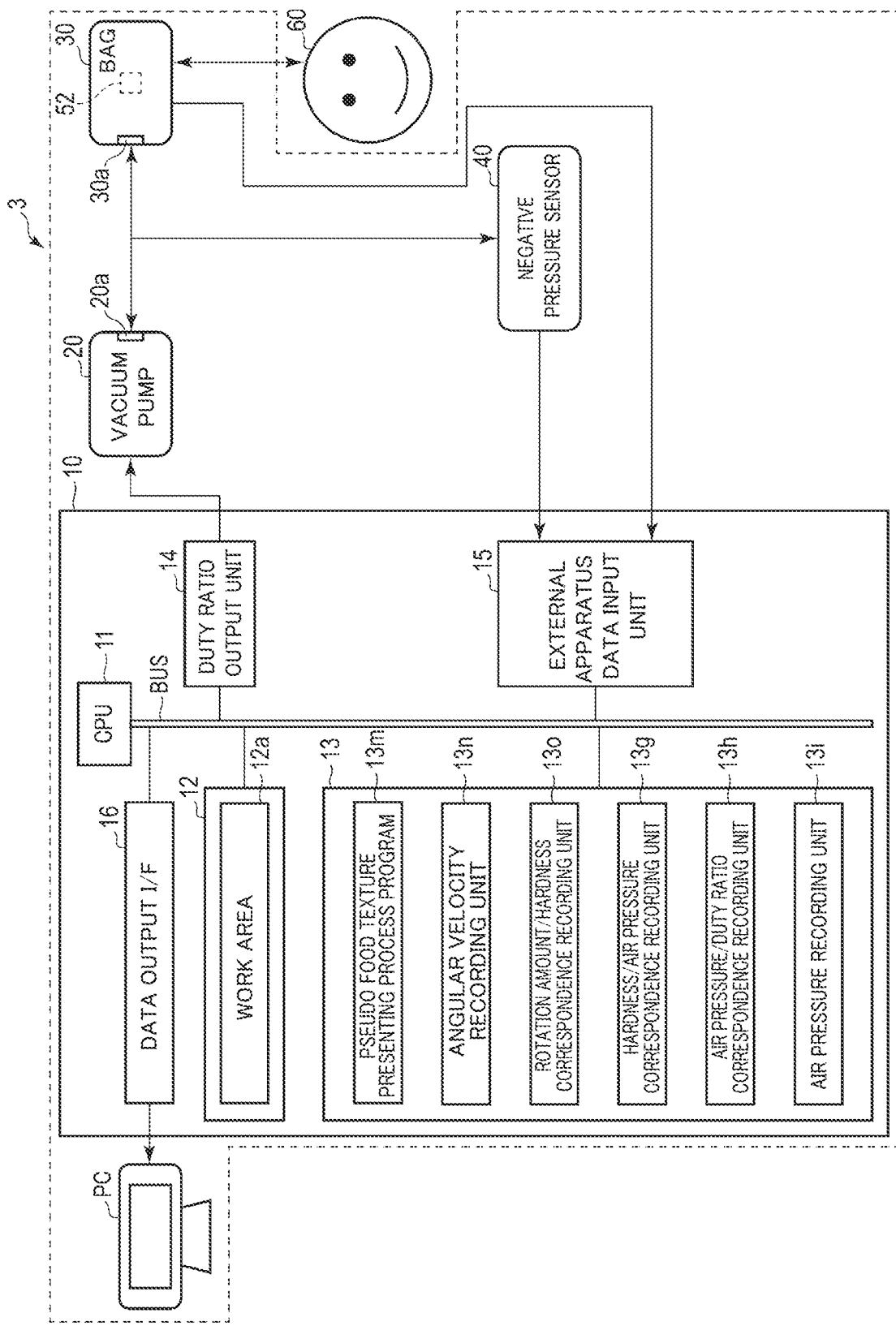
FIG. 14 is a block diagram showing a configuration of a mock food texture presenting apparatus according to a third embodiment.

FIG. 14 schematically shows a configuration of a mock food texture presenting apparatus 3 according to the third embodiment. As shown in FIG. 14, the mock food texture presenting apparatus 3 includes the microcomputer 10, the vacuum pump 20, the bag 30, the negative pressure sensor 40, a gyroscope sensor 52, and the personal computer PC. In FIG. 14, constitutional elements that are the same as the constitutional elements shown in FIG. 2 are denoted with the same reference signs as those shown in FIG. 2, and descriptions of these constitutional elements are omitted.

The gyroscope sensor 52 is arranged at the center of the inside of the bag 30, for example. The gyroscope sensor 52 measures angular velocities about three mutually orthogonal axes (x axis, y axis, and z axis), and transmits, to the microcomputer 10, angular velocity data that includes measurement values of the angular velocities about the three axes and a measurement time. The gyroscope sensor 52 acquires measurement values at predetermined time intervals (for example, intervals of 1 millisecond) and outputs angular velocity data in real time.

The recording unit 13 in the microcomputer 10 includes a program area in which a mock food texture presenting process program 13m is stored, an angular velocity recording unit 13n, a rotation amount/hardness correspondence recording unit 13o, the hardness/air pressure correspondence recording unit 13g, the air pressure/duty ratio correspondence recording unit 13h, and the air pressure recording unit 13i.

The mock food texture presenting process program 13m is executed by the CPU 11 using the work area 12a. When executed by the CPU 11, the mock food texture presenting process program 13m causes the CPU 11 to perform a mock food texture presenting process, which will be described later.

The angular velocity recording unit 13n records measurement values of the angular velocities acquired using the gyroscope sensor 52. In the angular velocity recording unit 13n, measurement values of the angular velocities are recorded in association with a measurement time.

A correspondence table (database) in which a rotation amount of the bag 30 is associated with the hardness of the bag 30 is recorded in the rotation amount/hardness correspondence recording unit 13o in advance. The correspondence table is set such that, as the rotation amount of the bag 30 is increased, the hardness of the bag 30 is reduced, for example. The rotation amount may be a rotation angle or the number of rotations, for example. In the present embodiment, the rotation amount is the rotation angle. When $\theta$ represents the rotation angle, the hardness is set to Stage 7 when $0° \leq \theta < \theta_1$, Stage 6 when $\theta_1 \leq \theta < \theta_2$, Stage 5 when $\theta_2 \leq \theta < \theta_3$, Stage 4 when $\theta_3 \leq \theta < \theta_4$, Stage 3 when $\theta_4 \leq \theta \leq \theta_5$, Stage 2 when $\theta_5 \leq \theta < \theta_6$, and Stage 1 when $\theta_6 \leq \theta$, for example. Here, specific angles [deg] are set for $\theta_1$ to $\theta_6$. Note that stages to which the hardness of the bag 30 is to be varied may be determined by performing an experiment that is similar to the experiment described in the first embodiment to identify a combination of stages between which a hardness difference can be sensed when the bag 30 is rotated within the mouth.

Figure 15:
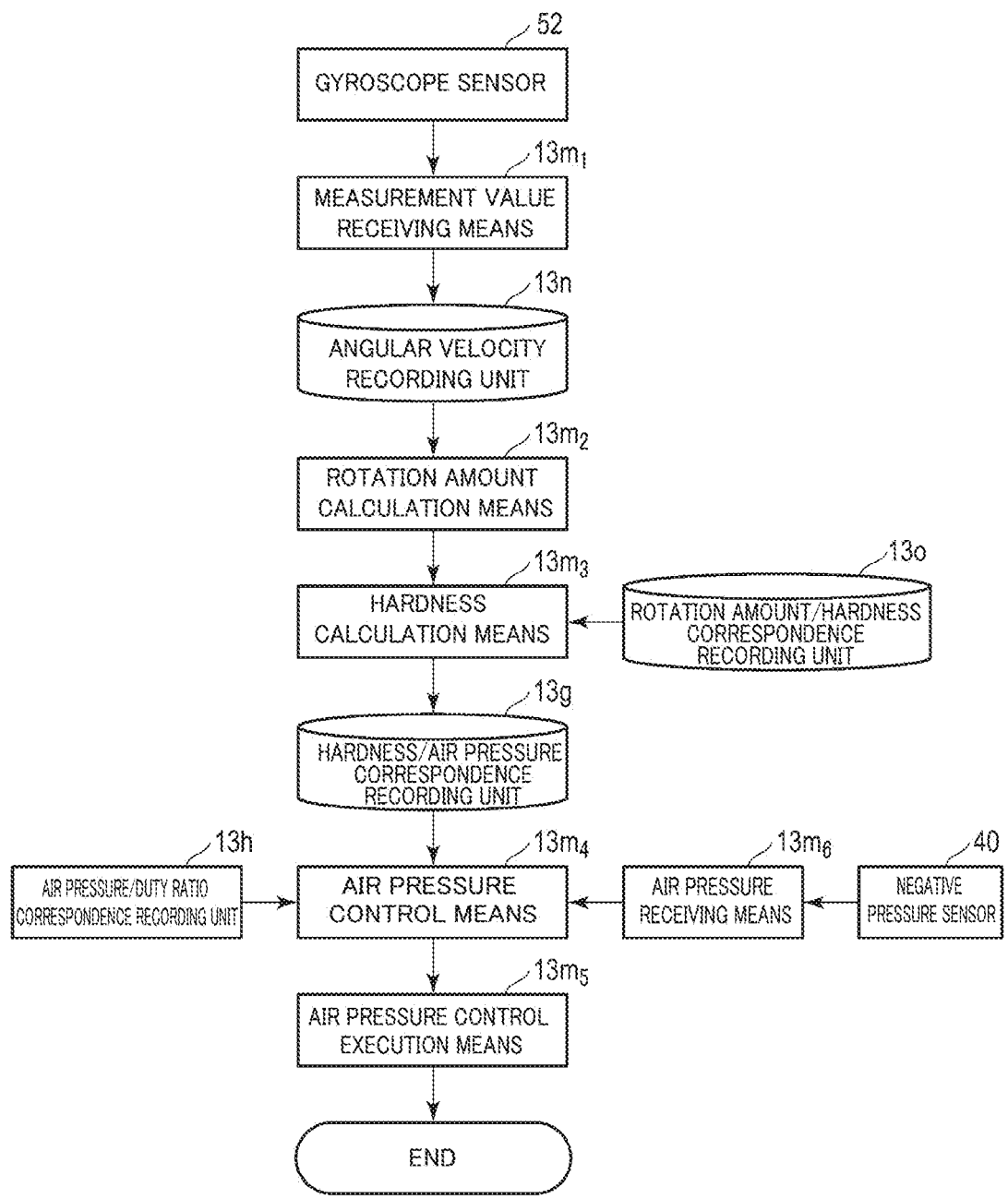
FIG. 15 is a block diagram showing a mock food texture presenting process realized by the mock food texture presenting apparatus shown in FIG. 14.

FIG. 15 schematically shows a mock food texture presenting process according to the present embodiment. The mock food texture presenting process shown in FIG. 15 is realized as a result of the CPU 11 in the microcomputer 10 executing the mock food texture presenting process program 13m. The CPU 11 functions as measurement value receiving means $13m_1$, rotation amount calculation means $13m_2$, hardness calculation means $13m_3$, air pressure control means $13m_4$, and air pressure control execution means $13m_5$, following the mock food texture presenting process program $13m$.

The measurement value receiving means $13m_1$ receives angular velocity data from the gyroscope sensor 52 via the external apparatus data input unit 15, and records the received angular velocity data in the angular velocity recording unit $13n$.

The rotation amount calculation means $13m_2$ calculates the rotation amount of the bag 30 based on the angular velocity data received by the measurement value receiving means $13m_1$. The rotation amount calculation means $13m_2$ calculates rotation angles of the x axis, the y axis, and the z axis by integrating absolute values of the angular velocities about the respective axes, for example. The sum of the thus obtained rotation angles of the x axis, the y axis, and the z axis is calculated as the rotation amount of the bag 30. In the present embodiment, the rotation amount is the amount by which the bag 30 is rotated after put into the mouth of the user 60, for example, and the interval of integration is from a point in time when the user 60 put the bag 30 into their mouth to a current point in time. The CPU 11 may further function as means for determining that the bag 30 is put into the mouth of the user 60. It is possible to determine that the bag 30 is put into the mouth of the user 60 based on input from the user or a sensor that is provided on the bag 30. For example, the CPU 11 may determine that the bag 30 is put into the mouth of the user 60 in response to a hardware button (not shown) provided in the microcomputer 10 being pressed by the user 60. Alternatively, a configuration is also possible in which a moisture sensor is provided on the bag 30, and the CPU 11 determines that the bag 30 is put into the mouth of the user 60 in response to a measurement value of the moisture amount received from the moisture sensor exceeding a threshold value.

Based on the correspondence table recorded in the rotation amount/hardness correspondence recording unit $13o$, the hardness calculation means $13m_3$ calculates the hardness of the bag 30 according to the rotation amount calculated by the rotation amount calculation means $13m_2$.

The air pressure control means $13m_4$ and the air pressure control execution means $13m_5$ respectively perform the same processes as the above-described air pressure control means $13b_4$ and the air pressure control execution means $13b_5$ (FIG. 8). Therefore, descriptions of the air pressure control means $13m_4$ and the air pressure control execution means $13m_5$ are omitted.

Note that the CPU 11 may further function as air pressure receiving means $13m_6$ following the mock food texture presenting process program $13m$. The air pressure receiving means $13m_6$ performs the same process as the above-described air pressure receiving means $13b_6$ (FIG. 8). Therefore, a description of the air pressure receiving means $13m_6$ is omitted.

Namely, the process for controlling the density of the powder or granular material in the bag 30 to realize the hardness calculated by the hardness calculation means $13m_3$ is common between the first embodiment and the third embodiment.

The mock food texture presenting apparatus 3 measures the amount of rotation of the bag 30 in the mouth of the user 60, and controls the density of the powder or granular material based on the measured rotation amount such that the bag 30 has a degree of hardness according to the measured rotation amount. The correspondence table recorded in the rotation amount/hardness correspondence recording unit $13o$ may be set such that, as the rotation amount of the bag 30 is increased, the hardness of the bag 30 is reduced, for example. In this case, it is possible to present texture of a food the entirety of which continuously becomes soft as rolled in the mouth, for example.

In the above-described example, the enclosing body is constituted by the single bag 30. Alternatively, the enclosing body may also be constituted by a plurality of bags. The enclosing body may have any one of the above-described first structure, second structure, and third structure.

If the enclosing body has the first structure, for example, the gyroscope sensor 52 may be arranged in any one of the plurality of bags. The rotation amount of each bag is calculated based on the rotation angle about at least one axis of the three axes depending on the arrangement relationship between the bags. For example, the rotation amount of a bag is calculated based on a measurement value of the angular velocity about the x axis, and the rotation amount of another bag is calculated based on a measurement value of the angular velocity about the y axis and a measurement value of the angular velocity about the z axis. The CPU 11 calculates the rotation amount with respect to each bag, and controls the hardness of each bag based on a calculation result. In this case, it is possible to present texture of a food in which only a portion extending along an axis of a rotation direction becomes soft, for example.

Fourth Embodiment

Figure 16:
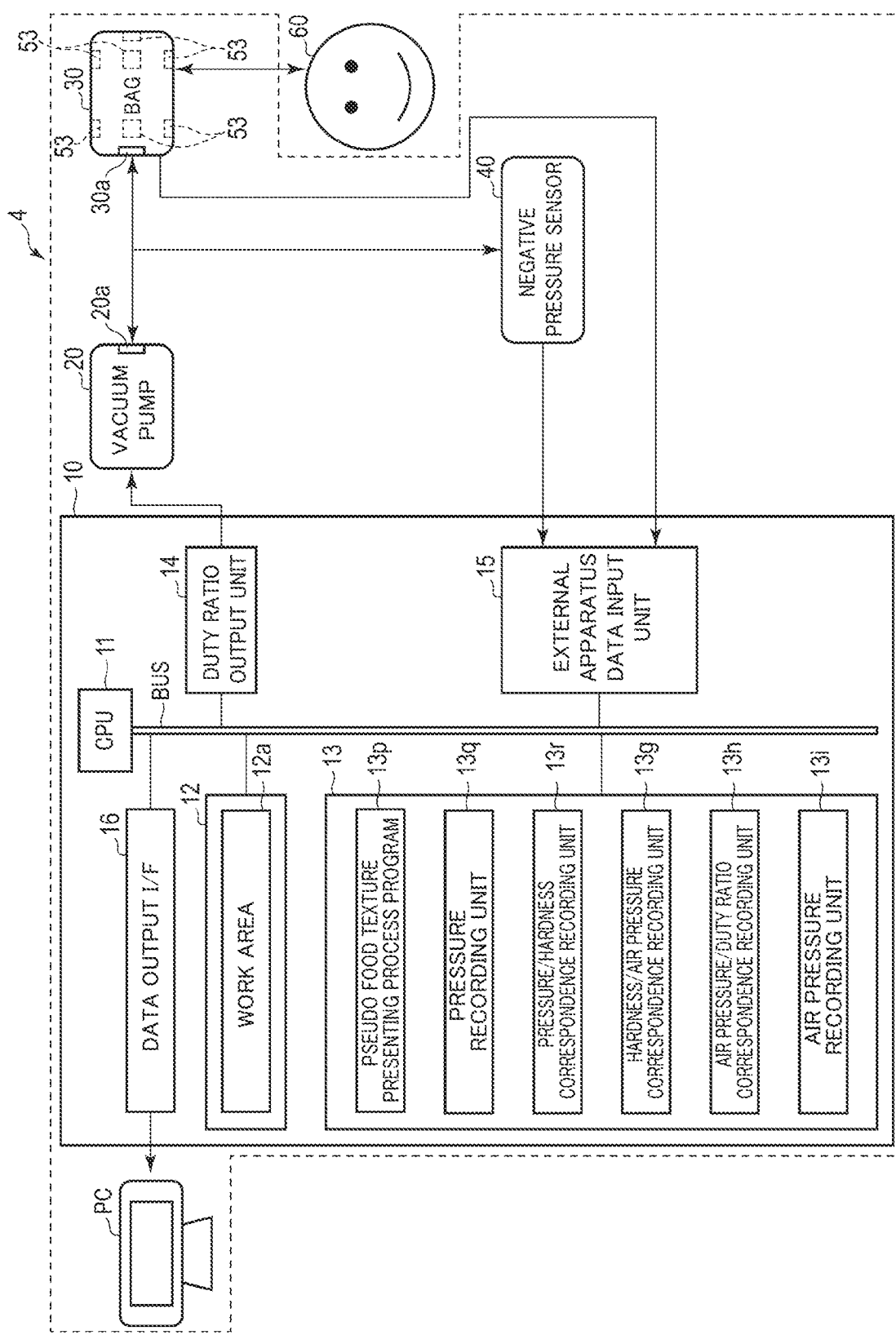
FIG. 16 is a block diagram showing a configuration of a mock food texture presenting apparatus according to a fourth embodiment.

FIG. 16 schematically shows a configuration of a mock food texture presenting apparatus 4 according to the fourth embodiment. As shown in FIG. 16, the mock food texture presenting apparatus 4 includes the microcomputer 10, the vacuum pump 20, the bag 30, the negative pressure sensor 40, a plurality of pressure sensors 53, and the personal computer PC. In FIG. 16, constitutional elements that are the same as the constitutional elements shown in FIG. 2 are denoted with the same reference signs as those shown in FIG. 2, and descriptions of these constitutional elements are omitted.

The plurality of pressure sensors 53 are arranged at a plurality of positions (sensor positions) on the inner surface of the bag 30. The pressure sensors 53 measure pressure applied to the sensor positions of the bag 30 from the outside, and transmit pressure data that includes measurement values of the pressure and a measurement time to the microcomputer 10. Each pressure sensor 53 acquires measurement values at predetermined time intervals (for example, intervals of 10 milliseconds) and outputs pressure data in real time.

The recording unit 13 in the microcomputer 10 includes a program area in which a mock food texture presenting process program $13p$ is stored, a pressure recording unit $13q$, a pressure/hardness correspondence recording unit $13r$, the hardness/air pressure correspondence recording unit $13g$, the air pressure/duty ratio correspondence recording unit $13h$, and the air pressure recording unit $13i$.

The mock food texture presenting process program $13p$ is executed by the CPU 11 using the work area $12a$. When executed by the CPU 11, the mock food texture presenting process program $13p$ causes the CPU 11 to perform a mock food texture presenting process, which will be described later.

The pressure recording unit $13q$ records measurement values of pressure acquired using the plurality of pressure sensors 53. In the pressure recording unit $13q$, measurement values of pressure are recorded in association with time information and identification information for identifying the pressure sensors 53.

A correspondence table (database) in which external pressure, which is pressure applied to the bag 30 from the outside, is associated with the hardness of the bag 30 is recorded in the pressure/hardness correspondence recording unit 13$r$ in advance. The correspondence table is set such that, as the external pressure is increased, the hardness of the bag 30 is reduced, for example. For example, when P represents the external pressure, the hardness is set to Stage 7 when $0 \leq P < P_1$, Stage 6 when $P_1 \leq P < P_2$, Stage 5 when $P_2 \leq P < P_3$, Stage 4 when $P_3 \leq P < P_4$, Stage 3 when $P_4 \leq P < P_5$, Stage 2 when $P_5 \leq P < P_6$, and Stage 1 when $P_6 \leq P$. Here, specific pressure values are set for $P_1$ to $P_6$. Note that stages to which the hardness of the bag 30 is to be varied may be determined by performing an experiment that is similar to the experiment described in the first embodiment to identify a combination of stages between which a hardness difference can be sensed when the bag 30 is sandwiched using teeth, lips, or the tongue, or is pressed using the tongue.

Figure 17:
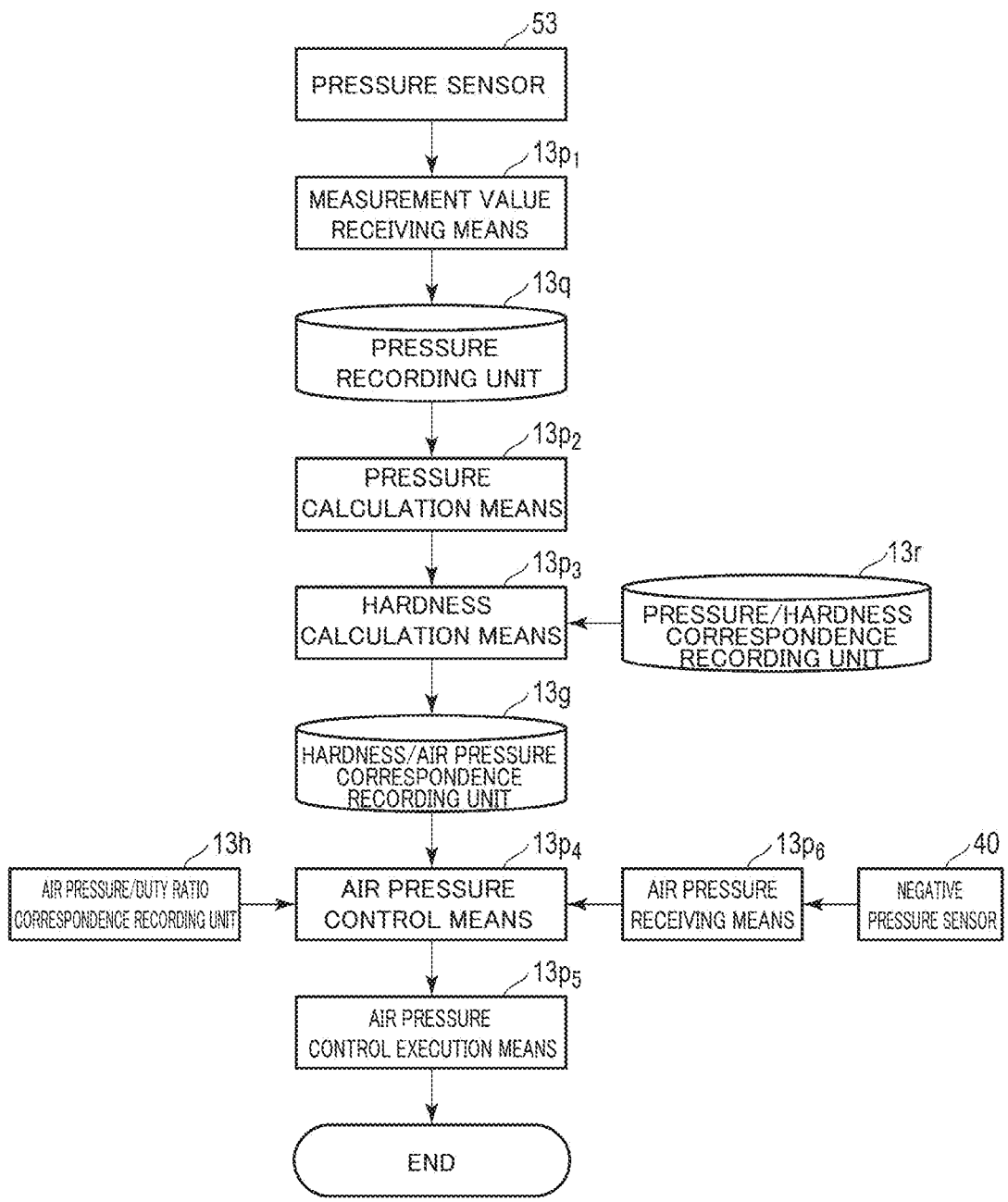
FIG. 17 is a block diagram showing a mock food texture presenting process realized by the mock food texture presenting apparatus shown in FIG. 16.

FIG. 17 schematically shows a mock food texture presenting process according to the present embodiment. The mock food texture presenting process shown in FIG. 17 is realized as a result of the CPU 11 in the microcomputer 10 executing the mock food texture presenting process program 13$p$. The CPU 11 functions as measurement value receiving means 13$p_1$, pressure calculation means 13$p_2$, hardness calculation means 13$p_3$, air pressure control means 13$p_4$, and air pressure control execution means 13$p_5$, following the mock food texture presenting process program 13$p$.

The measurement value receiving means 13$p_1$ receives pressure data from the plurality of pressure sensors 53 via the external apparatus data input unit 15, and records the received pressure data in the pressure recording unit 13$q$.

The pressure calculation means 13$p_2$ calculates the external pressure applied to the bag 30 from the outside, based on the measurement data received by the measurement value receiving means 13$p_1$. For example, the pressure calculation means 13$p_2$ calculates, as the external pressure, the largest pressure measurement value of a plurality of pressure measurement values measured at a time t. In another example, the pressure calculation means 13$p_2$ may also calculate, as the external pressure, the sum or an average of the plurality of pressure measurement values measured at the time t. In yet another example, the pressure calculation means 13$p_2$ may also integrate (accumulate) pressure measurement values with respect to each pressure sensor 53, and calculate the largest integrated value (accumulated value) of integrated values obtained for the respective sensors 53, as the external pressure.

Based on the correspondence table recorded in the pressure/hardness correspondence recording unit 13$r$, the hardness calculation means 13$p_3$ calculates the hardness of the bag 30 according to the external pressure calculated by the pressure calculation means 13$p_2$.

The air pressure control means 13$p_4$ and the air pressure control execution means 13$p_5$ respectively perform the same processes as the above-described air pressure control means 13$b_4$ and the air pressure control execution means 13$b_5$ (FIG. 8). Therefore, descriptions of the air pressure control means 13$p_4$ and the air pressure control execution means 13$p_5$ are omitted.

Note that the CPU 11 may further function as air pressure receiving means 13$p_6$ following the mock food texture presenting process program 13$p$. The air pressure receiving means 13$p_6$ performs the same process as the above-described air pressure receiving means 13$b_6$ (FIG. 8). Therefore, a description of the air pressure receiving means 13$p_6$ is omitted.

Namely, the process for controlling the density of the powder or granular material in the bag 30 to realize the hardness calculated by the hardness calculation means 13$p_3$ is common between the first embodiment and the fourth embodiment.

The mock food texture presenting apparatus 4 measures the external pressure applied to the bag 30 from the outside, and controls the density of the powder or granular material based on the measured external pressure such that the bag 30 has a degree of hardness according to the measured external pressure. The correspondence table recorded in the pressure/hardness correspondence recording unit 13$r$ may be set such that, as the external pressure is increased, the hardness of the bag 30 is reduced, for example. In this case, it is possible to present texture of a food the entirety of which continuously becomes soft as a force with which the food is sandwiched or pressed in the mouth is increased, for example.

Although it is desirable to provide the bag 30 with a plurality of pressure sensors 53 as is the case with the above-described example, a configuration is also possible in which the bag 30 is provided with only one pressure sensor 53.

In the above-described example, the enclosing body is constituted by the single bag 30. Alternatively, the enclosing body may also be constituted by a plurality of bags. The enclosing body may have any one of the above-described first structure, second structure, and third structure.

If the enclosing body has the first structure, for example, the pressure sensors 53 are arranged in each of the plurality of bags. The CPU 11 measures the external pressure with respect to each bag and controls the hardness of each bag based on a measurement result. In this case, it is possible to present texture of a food in which only a position that is sandwiched or pressed with a strong force becomes soft, for example.

The present invention is not limited to the above-described embodiments, and various alterations can be made within a scope not departing from the gist of the present invention when the present invention is implemented. Furthermore, the above-described embodiments include inventions in various stages, and various inventions can be extracted by appropriately combining a plurality of disclosed constitutional elements. For example, even if some constitutional elements are omitted from all constitutional elements shown in the embodiments or some constitutional elements are combined in a different manner, a configuration obtained by omitting or combining the constitutional elements can be extracted as an invention so long as the issues described in Technical Problem can be solved and the effects described in Effects of the Invention can be achieved.

REFERENCE SIGNS LIST

1 Mock food texture presenting apparatus
10 Microcomputer
11 CPU
12 RAM
12$a$ Work area
13 Recording unit
13$a$ Threshold value calculation program
13$a_1$ Minimum value measuring and recording means
13$a_2$ Maximum value measuring and recording means
13$a_3$ Threshold value calculating and recording means
13$b$ Mock food texture presenting process program $13b_1$ Measurement value receiving means
$13b_2$ Chewing number of times calculation means
$13b_3$ Hardness calculation means
$13b_4$ Air pressure control means
$13b_5$ Air pressure control execution means
$13b_6$ Air pressure receiving means
13c Distance recording unit
13d Maximum value/minimum value recording unit
13e Threshold value recording unit
13f Chewing number of times/hardness correspondence recording unit
13g Hardness/air pressure correspondence recording unit
13h Air pressure/duty ratio correspondence recording unit
13i Air pressure recording unit.
14 Duty ratio output unit
15 External apparatus data input unit
16 Data output I/F
20 Vacuum pump
20a Suction opening
30 Bag
30a Air opening
40 Negative pressure sensor
50 Photoreflector
60 User
GT1, GT2 Flexible tube
2 Mock food texture presenting apparatus
13j Mock food texture presenting process program
$13j_1$ Measurement value receiving means
$13j_2$ Number of times calculation means
$13j_3$ Hardness calculation means
$13j_4$ Air pressure control means
$13j_5$ Air pressure control execution means
$13j_6$ Air pressure receiving means
13k Moisture amount/pressure recording unit
13l Number of times/hardness correspondence recording unit
51 Sensor pair
51a Moisture sensor
51b Pressure sensor
3 Mock food texture presenting apparatus
13m Mock food texture presenting process program
$13m_1$ Measurement value receiving means
$13m_2$ Rotation amount calculation means
$13m_3$ Hardness calculation means
$13m_4$ Air pressure control means
$13m_5$ Air pressure control execution means
$13m_6$ Air pressure receiving means
13n Angular velocity recording unit
13o Rotation amount/hardness correspondence recording unit
52 Gyroscope sensor
4 Mock food texture presenting apparatus
13p Mock food texture presenting process program
$13p_1$ Measurement value receiving means
$13p_2$ Pressure calculation means
$13p_3$ Hardness calculation means
$13p_4$ Air pressure control means
$13p_5$ Air pressure control execution means
$13p_6$ Air pressure receiving means
13q Pressure recording unit
13r Pressure/hardness correspondence recording unit
53 Pressure sensor

The invention claimed is:

1. A mock food texture presenting apparatus comprising:
an enclosing body that encloses a powder or granular material and has hardness that varies according to an air pressure inside the enclosing body;
a computer including a processor configured to:
grasp conditions of chewing performed on the enclosing body by a user, wherein grasping the conditions of chewing comprises measuring a number of times of chewing performed on the enclosing body;
determine hardness of the enclosing body corresponding to the number of times of chewing, wherein as the number of times of chewing increases, the determined hardness of the enclosing body decreases;
determine an air pressure inside the enclosing body to achieve the determined hardness of the enclosing body; and
control density of the powder or granular material in the enclosing body based on adjusting a volume of air inside the enclosing body according to the determined air pressure.

2. The mock food texture presenting apparatus according to claim 1, wherein the computer is configured to measure the number of times of chewing performed on the enclosing body by the user based on conditions of actions of the user, and the computer is configured to control the density of the powder or granular material in the enclosing body according to the number of times of chewing.

3. The mock food texture presenting apparatus according to claim 2,
wherein
the number of times of chewing performed by the user and hardness of the enclosing body according to the number of times of chewing are recorded in association with each other in advance,
the computer is configured to extract, from a correspondence between the chewing number of times and the hardness of the enclosing body, the hardness of the enclosing body for which the user senses a change according to the number of times of chewing; and
wherein
the hardness of the enclosing body and the air pressure required to achieve the hardness of the enclosing body are recorded in association with each other, and
the computer is configured to select the air pressure from a correspondence between the hardness and the air pressure according to the extracted hardness, and control the air pressure inside the enclosing body to be the selected air pressure.

4. The mock food texture presenting apparatus according to claim 2, wherein measuring the number of times of chewing performed on the enclosing body comprises:
measuring a change of a position of a lower jaw of the user and measuring the number of times of chewing performed on the enclosing body by the user, based on the change of the position;
measuring, using a pressure sensor, pressure applied to a tooth or a jaw of the user and measuring the number of times of chewing performed on the enclosing body by the user, based on the pressure measured by the pressure sensor; and
measuring, using a pressure sensor, pressure applied to the enclosing body from outside and measuring the number of times of chewing performed on the enclosing body by the user, based on the pressure measured by the pressure sensor.

5. The mock food texture presenting apparatus according to claim 2, wherein measuring the number of times of chewing performed on the enclosing body comprises: measuring chewing sound generated as a result of the user chewing the enclosing body and measuring the number of times of chewing based on the chewing sound.

6. The mock food texture presenting apparatus according to claim 1, wherein the computer is configured to calculate hardness of the enclosing body based on any of: a change amount of a position of a lower jaw of the user per unit time; pressure applied to a tooth or a jaw of the user; pressure applied to the enclosing body from outside; and volume of chewing sound generated as a result of the enclosing body being chewed or a change amount of the chewing sound per unit time.

7. The mock food texture presenting apparatus according to claim 1, wherein the enclosing body has at least one of a first structure that is constituted by a plurality of bags, a second structure that is constituted by layered bags including an outer skin that covers an outer side and an inner skin that is entirely covered by the outer skin, and a third structure that is a combination of the first structure and the second structure, and the enclosing body controller controls an air pressure inside at least one bag that is included in the first to third structures.

8. The mock food texture presenting apparatus according to claim 7, wherein a powder or granular material that is enclosed in at least one bag of the plurality of bags or the layered bags included in the first to third structures differs from a powder or granular material that is enclosed in another bag of the plurality of bags or the layered bags.

9. The mock food texture presenting apparatus according to claim 7, wherein a material of at least one bag of the bags included in the first to third structures differs from a material of another bag of the bags.

10. The mock food texture presenting apparatus according to claim 1, wherein the computer is configured to control a change amount of the air pressure per unit time when controlling the air pressure inside the enclosing body.

11. The mock food texture presenting apparatus according to claim 1, wherein the air pressure inside the enclosing body controlled by the enclosing body controller has a value not larger than 0.

12. The mock food texture presenting apparatus according to claim 1, wherein the enclosing body is constituted by a deformable material, and the computer is further configured to calculate density of the powder or granular material in the enclosing body based on a capacity of the enclosing body in an initial state, a volume of the powder or granular material enclosed in the enclosing body, and a volume of the powder or granular material and air that are introduced into or discharged from the enclosing body.

13. The mock food texture presenting apparatus according to claim 12, the computer is configured to maintain a shape of the enclosing body by fixing at least one of the capacity of the enclosing body, the volume of the powder or granular material enclosed in the enclosing body, and the air pressure inside the enclosing body.

14. A method for presenting mock food texture to be executed by a computer, the method comprising:
grasping conditions of chewing performed by a user on an enclosing body that encloses a powder or granular material, wherein grasping the conditions of chewing comprises measuring a number of times of chewing performed on the enclosing body;
determining hardness of the enclosing body corresponding to the number of times of chewing, wherein as the number of times of chewing increases, the determined hardness of the enclosing body decreases;
determining an air pressure inside the enclosing body to achieve the determined hardness of the enclosing body; and
controlling density of the powder or granular material in the enclosing body based on adjusting a volume of air inside the enclosing body according to the determined air pressure.

15. The mock food texture presenting apparatus according to claim 1, wherein the enclosing body has at least one of a first structure that is constituted by a plurality of bags, a second structure that is constituted by layered bags including an outer skin that covers an outer side and an inner skin that is entirely covered by the outer skin, and a third structure that is a combination of the first structure and the second structure.

16. The mock food texture presenting apparatus according to claim 15, having at least one of the following features: a powder or granular material that is enclosed in at least one bag of the plurality of bags or the layered bags included in the first to third structures differs from a powder or granular material that is enclosed in another bag of the plurality of bags or the layered bags; and a material of at least one bag of the bags differs from a material of another bag of the bags.

17. The mock food texture presenting apparatus according to claim 1, wherein the computer is configured to measure the number of times the user has licked the enclosing body with their tongue; and wherein the computer is configured to control density of the powder or granular material in the enclosing body according to the measured number of times.

18. The mock food texture presenting apparatus according to claim 1, wherein the computer is configured to measure one of a rotation amount of the enclosing body or pressure applied to the enclosing body from outside; and wherein the computer is configured to control density of the powder or granular material in the enclosing body according to one of the measured rotation amount or the pressure applied to the enclosing body.

19. The method for presenting mock food texture according to claim 14, the method further comprising: measuring one of (1) the number of times a user has licked, with their tongue, the enclosing body, (2) a rotation amount of the enclosing body, or (3) pressure applied to the enclosing body; and controlling density of the powder or granular material in the enclosing body according to one of the measured number of times the user has licked, the measured rotation amount, or the measured pressure.

20. A non-transitory computer readable medium storing instructions causing a computer to execute:
grasping conditions of chewing performed by a user on an enclosing body that encloses a powder or granular material, wherein grasping the conditions of chewing comprises measuring a number of times of chewing performed on the enclosing body;
determining hardness of the enclosing body corresponding to the number of times of chewing, wherein as the number of times of chewing increases, the determined hardness of the enclosing body decreases;
determining an air pressure inside the enclosing body to achieve the determined hardness of the enclosing body; and
controlling density of the powder or granular material in the enclosing body based on adjusting a volume of air inside the enclosing body according to the determined air pressure.

* * * * *